United States Patent
Vogelstein et al.

(10) Patent No.: US 9,315,868 B2
(45) Date of Patent: Apr. 19, 2016

(54) DIAGNOSTIC METHOD USING PALB2

(75) Inventors: Bert Vogelstein, Baltimore, MD (US); Kenneth W. Kinzler, Baltimore, MD (US); D. Williams Parsons, Ellicott City, MD (US); Sian Jones, Baltimore, MD (US); Scott Kern, Hunt Valley, MD (US); Ralph Hruban, Baltimore, MD (US); James R. Eshleman, Lutherville, MD (US); Michael Goggins, Baltimore, MD (US); Alison Klein, Baltimore, MD (US); Manuel Hidalgo, Baltimore, MD (US); Victor E. Velculescu, Dayton, MD (US)

(73) Assignee: The Johns Hopkins University, Baltimore, MD (US)

( * ) Notice: Subject to any disclaimer, the term of this patent is extended or adjusted under 35 U.S.C. 154(b) by 141 days.

(21) Appl. No.: 13/254,610

(22) PCT Filed: Mar. 5, 2010

(86) PCT No.: PCT/US2010/026290
§ 371 (c)(1),
(2), (4) Date: Oct. 28, 2011

(87) PCT Pub. No.: WO2010/102160
PCT Pub. Date: Sep. 10, 2010

(65) Prior Publication Data
US 2012/0034318 A1      Feb. 9, 2012

Related U.S. Application Data

(60) Provisional application No. 61/157,700, filed on Mar. 5, 2009, provisional application No. 61/264,019, filed on Nov. 24, 2009.

(51) Int. Cl.
C12Q 1/68      (2006.01)
C12P 19/34     (2006.01)
A61P 35/00     (2006.01)
G01N 33/574    (2006.01)
C07H 21/04     (2006.01)

(52) U.S. Cl.
CPC ........ *C12Q 1/6886* (2013.01); *G01N 33/57438* (2013.01); *C12Q 2600/106* (2013.01); *C12Q 2600/156* (2013.01)

(58) Field of Classification Search
CPC ........... C12Q 1/6886; C12Q 2600/156; C12Q 2600/106; G01N 33/57438; G01N 2800/50
See application file for complete search history.

(56) References Cited

FOREIGN PATENT DOCUMENTS

WO      2008047128 A2      4/2008

OTHER PUBLICATIONS

Abbott D.W. et al. Journal of the National Cancer Institute, vol. 90, No. 13, Jul. 1, 1998, pp. 978-985.*
Helleday T. et al. DNA Repair 6 (2007) 923-935.*
Lord C.J. et al. Current Opinion in Pharmacology 2008, 8:363-369.*
Helleday T. et al. Nature Reviews—Cancer (Mar. 2008) vol. 8, pp. 193-204.*
Rahman N. et al Nature Genetics, (Feb. 2007) vol. 39, No. 2, pp. 165-167).*
The Breast Cancer Linkage Consortium (1999) Journal of the National Cancer Institute, vol. 91, No. 15, pp. 1310-1316.*
Jones et al., "Exomic sequencing identifies PALB2 as a pancreatic cancer susceptibility gene" Science, vol. 324, No. 5924, p. 217, Mar. 5, 2009 (Epub).
Cao et al., "The prevalence of PALB2 aermline mutations in BRCA1/BRCA2 negative Chinese woman with early onset breast cancer or affected relatives", Breast Cancer Res Treat, vol. 114, No. 3 pp. 457-462, Apr. 30, 2008 (Epub).
Tischkowitz et al., "Analysis of the gene coding for the BRCA2-interacting protein PALB2 in hereditary prostate cancer", Prostate, vol. 68, No. 6, pp. 675-678, Feb. 20, 2008, (Epub).
Tischkowitz et al., "Analysis of PALB2/FANCN-associated breast cancer families", Proc Natl Acad Sci USA, vol. 104, No. 16, pp. 6788-6793, Apr. 9, 2007 (Epub).
Erkko et al., "A recurrent mutation in PALB2 in Finnish cancer families", Nature, vol. 446, No. 7133, pp. 316-319, Feb. 7, 2007
Pylkas et al., "Analysis of large deletions in BRCA1, BRCA2 and PALB2 genes in Finnish breast and ovarian cancer families", BMC Cancer, vol. 8, 146, May 26, 2008.
International Search Report for PCT/US2010/026290 dated Nov. 18, 2010.
Office Action issued in related Canadian Application No. 2,754,199, dated Jul. 15, 2015.
Jimeno et al., "Molecular Biomarkers: their Increasing Role in the Diagnosis Characterization and Therapy Guidance in Pancreatic Cancer," Molecular Cancer Therapy, 5/4, pp. 787-796, Apr. 1, 2006.

* cited by examiner

*Primary Examiner* — Stephen Kapushoc
(74) *Attorney, Agent, or Firm* — Banner & Witcoff, Ltd.

(57) ABSTRACT

The present invention provides a method for detecting mutations in the PALB2 gene in pancreatic cancer patients and in individuals having a family history of pancreatic cancer. Methods are also provided for diagnosing a predisposition to pancreatic cancer, for predicting a patient's response to pancreatic cancer therapies, and for treating pancreatic cancer, based on presence of a PALB2 mutation or abberant PALB2 gene expression in a patient.

7 Claims, 4 Drawing Sheets

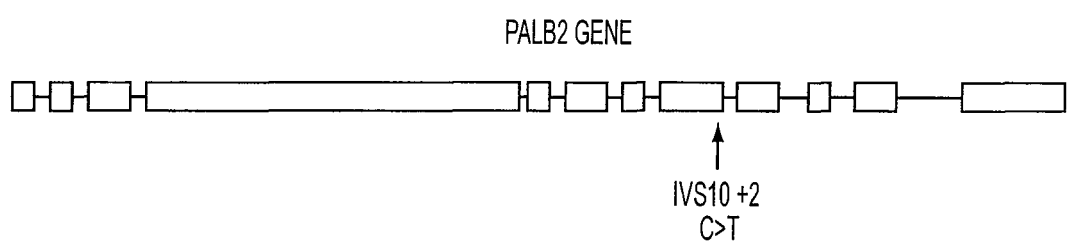
FIG. 4A
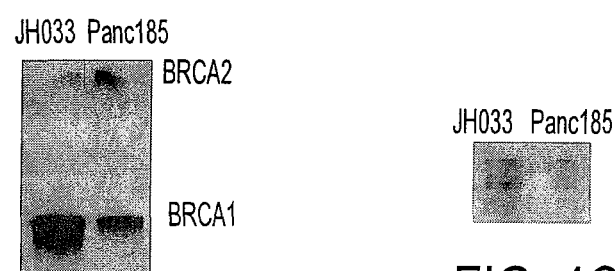
FIG. 4B
FIG. 4C

SEQUENCE LISTING

```
<160> NUMBER OF SEQ ID NOS: 8

<210> SEQ ID NO 1
<211> LENGTH: 48
<212> TYPE: DNA
<213> ORGANISM: Homo sapiens

<400> SEQUENCE: 1
aaaacagtag aagaacaaga ttgtctcagc aggatctctc accgcagc                48
```

<210> SEQ ID NO 2
<211> LENGTH: 48
<212> TYPE: DNA
<213> ORGANISM: Homo sapiens

<400> SEQUENCE: 2
ttatgaacaa cattgttatt tggatttaaa aactggtcaa ctcctgaa                48

<210> SEQ ID NO 3
<211> LENGTH: 49
<212> TYPE: DNA
<213> ORGANISM: Homo sapiens

<400> SEQUENCE: 3
tgtgccaaag agagtgagtc gttgtgaagc cctgtgtttc agctcattg               49

<210> SEQ ID NO 4
<211> LENGTH: 49
<212> TYPE: DNA
<213> ORGANISM: Homo sapiens

<400> SEQUENCE: 4
aatgatgtga cttttgtttt cacatactga aacagcagag cttcctgct               49

<210> SEQ ID NO 5
<211> LENGTH: 49
<212> TYPE: DNA
<213> ORGANISM: Homo sapiens

<400> SEQUENCE: 5
attatgaaca acattgttat ttggcaagct ttccctctag gtcctcagt               49

<210> SEQ ID NO 6
<211> LENGTH: 4069
<212> TYPE: DNA
<213> ORGANISM: Homo sapiens

<400> SEQUENCE: 6
gcaggccgaa tggtggattt aattggccgg agtttagggc gcgcttggcc cgcgtgggtc    60
agctgatcgc gcactgaggg tgcgatcccg ggctccccat tccttcctgg ggcgcctccc   120
cggcccaggg ccaactgggt cccggtgtcg gcaggcctgg ggtcggcgac ggctgctctt   180
ttcgttctgt cgcctgcccg atggacgagc ctcccgggaa gcccctcagc tgtgaggaga   240
aggaaaagtt aaaggagaaa ttagcattct tgaaaaggga atacagcaag acactagccc   300
gccttcagcg tgcccaaaga gctgaaaaga ttaagcattc tattaagaaa acagtagaag   360
aacaagattg tttgtctcag caggatctct caccgcagct aaaacactca gaacctaaaa   420
ataaaatatg tgtttatgac aagttacaca tcaaaaccca tcttgatgaa gaaactggag   480
aaaagacatc tatcacactt gatgttgggc ctgagtcctt taaccctgga gatgcccag    540 gaggattacc tatacaaaga acagatgaca cccaagaaca ttttccccac agggtcagtg   600
accctagtgg tgagcaaaag cagaagctgc caagcagaag aaagaagcag cagaagagga   660
catttatttc acaggagaga gactgtgtct ttggcactga ttcactcaga ttgtctggga   720
aaagactaaa ggaacaggaa gaaatcagta gcaaaaatcc tgctagatca ccagtaactg   780
aaataagaac tcaccttta agtcttaaat ctgaacttcc agattctcca gaaccagtta   840
cagaaattaa tgaagacagt gtattaattc caccaactgc ccaaccagaa aaaggtgttg   900

```
atacattcct aagaagacct aatttcacca gggcgactac agttccttta cagactctat    960
cagatagcgg tagtagtcag caccttgaac acattcctcc taaaggtagc agtgaactta   1020
ctactcacga cctaaaaaac attagattta cttcacctgt aagtttggag cacaaggca   1080
aaaaaatgac tgtctctaca gataacctcc ttgtaaataa agctataagt aaaagtggcc   1140
aactgcccac aagttctaat ttagaggcaa atatttcatg ttctctaaat gaactcacct   1200
acaataactt accagcaaat gaaaccaaa acttaaaaga acaaaatcaa acagagaaat   1260
ctttaaaatc tcccagtgac actcttgatg gcaggaatga aaatcttcag gaaagtgaga   1320
ttctaagtca acctaagagt cttagcctgg aagcaacctc tcctcttcct gcagaaaaac   1380
attcttgcac agtgcctgaa ggccttctgt ttcctgcaga atattatgtt agaacaacac   1440
gaagcatgtc caattgccag aggaaagtag ccgtggaggc tgtcattcag agtcatttgg   1500
atgtcaagaa aaagggtttt aaaaataaaa ataaggatgc aagtaaaaat ttaaaccttt   1560
ccaatgagga aactgaccaa agtgaaatta ggatgtctgg cacatgcaca ggacaaccaa   1620
gttcaagaac ctctcagaaa cttctctcat taactaaagt cagctctccc gctgggccca   1680
ctgaagataa tgacttgtct aggaaggcag ttgcccaagc acctggtaga agatacacag   1740
gaaaagaaa atcagcctgc acccccagcat cagatcattg tgaaccactt ttgccaactt   1800
ctagcctgtc gattgttaac aggtccaagg aagaagtcac ctcacacaaa tatcagcacg   1860
aaaaattatt tattcaagtg aaagggaaga aaagtcgtca tcaaaagag gattcccttt   1920
cttggagtaa tagtgcttat ttatccttgg atgatgatgc tttcacggct ccatttcata   1980
gggatggaat gctgagttta aagcaactac tgtcttttct cagtatcaca gactttcagt   2040
tacctgatga agactttgga cctcttaagc ttgaaaaagt gaagtcctgc tcagaaaaac   2100
cagtggagcc ctttgagtca aaaatgtttg gagagagaca tcttaaagag gaagctgta   2160
ttttccaga ggaactgagt cctaaacgca tggatacaga aatggaggac ttagaagagg   2220
acctattgt tctaccagga aaatcacatc ccaaaaggcc aaactcgcaa agccagcata   2280
caaagacggg cctttcttca tccatattac tttatactcc tttaaatacg gttgcgcctg   2340
atgataatga caggcctacc acagacatgt gttcacctgc tttccccatc ttaggtacta   2400
ctccagcctt tggccctcaa ggctcctatg aaaaagcatc tacagaagtt gctggacgaa   2460
cttgctgcac acccccaactt gctcatttga aagactcagt ctgtcttgcc agtgatacta   2520
aacaattcga cagttcaggc agcccagcaa aaccacatac caccctgcaa gtgtcaggca   2580
ggcaaggaca acctacctgt gactgtgact ctgtcccgcc aggaacacct ccacccattg   2640
agtcattcac tttaagaa aatcagctct gtagaaacac atgccaggag ctgcataaac   2700
attccgtcga acagactgaa acagcagagc ttcctgcttc tgatagcata aacccaggca   2760
acctacaatt ggtttcagag ttaaagaatc cttcaggttc ctgttccgta gatgtgagtg   2820
ccatgttttg ggaaagagcc ggttgtaaag agccatgtat cataactgct tgcgaagatg   2880
tagtttctct ttggaaagct ctggatgctt ggcagtggga aaaactttat acctggcact   2940
tcgcagaggt tccagtatta cagatagttc cagtgcctga tgtgtataat ctcgtgtgtg   3000
tagctttggg aaatttggaa atcagagaga tcagggcatt gttttgttcc tctgatgatg   3060
aaagtgaaaa gcaagtacta ctgaagtctg gaaatataaa agctgtgctt ggcctgacaa   3120
agaggaggct agttagtagc agtgggaccc tttctgatca acaagtagaa gtcatgacgt   3180
ttgcagaaga tggaggaggc aaagaaaacc aattttgat gccccctgag gagactatac   3240
taacttttgc tgaggtccaa gggatgcaag aagctctgct tggtactact attatgaaca   3300
```

```
acattgttat ttggaattta aaaactggtc aactcctgaa aaagatgcac attgatgatt    3360
cttaccaagc ttcagtctgt cacaaagcct attctgaaat ggggcttctc tttattgtcc    3420
tgagtcatcc ctgtgccaaa gagagtgagt cgttgcgaag ccctgtgttt cagctcattg    3480
tgattaaccc taagacgact ctcagcgtgg gtgtgatgct gtactgtctt cctccagggc    3540
aggctggcag gttcctggaa ggtgacgtga agatcactg tgcagcagca atcttgactt     3600
ctggaacaat tgccatttgg gacttacttc tcggtcagtg tactgccctc ctcccacctg    3660
tctctgacca acattggtct tttgtgaaat ggtcgggtac agactctcat tgctggctg     3720 gacaaaaaga tggaaatata tttgtatacc actattcata agttaggta aagtgaaaac     3780 acaattttct ggatatattg ggcctcttag tatttttttgg agttttaaat ataaaggaga   3840
atatctgaat gacacttaaa atgattgctt gtttatgtcc agacagactt attttttatt    3900
ctaatgatgg tagcaccact gatcttggat gtacatttat gtatactttg agaaaagggg   3960
ttttaggttg attttttgtaa tttcccacat ttgtacatgt gcttttaaag gtgtacataa   4020
agcttcaaat ggcaataaat atttatttttt atacattcaa aaaaaaaa               4069

<210> SEQ ID NO 7
<211> LENGTH: 3561
<212> TYPE: DNA
<213> ORGANISM: Homo sapiens

<400> SEQUENCE: 7
atggacgagc ctcccgggaa gcccctcagc tgtgaggaga aggaaaagtt aaaggagaaa      60
ttagcattct tgaaaaggga atacagcaag acactagccc gccttcagcg tgcccaaaga     120
gctgaaaaga ttaagcattc tattaagaaa acagtagaag aacaagattg tttgtctcag     180
caggatctct caccgcagct aaaacactca gaacctaaaa ataaaatatg tgtttatgac     240
aagttacaca tcaaaaccca tcttgatgaa gaaactggag aaaagacatc tatcacactt     300
gatgttgggc ctgagtcctt taaccctgga gatggcccag gaggattacc tatacaaaga     360
acagatgaca cccaagaaca ttttcccac agggtcagtg accctagtgg tgagcaaaag     420
cagaagctgc caagcagaag aaagaagcag cagaagagga catttatttc acaggagaga    480
gactgtgtct ttggcactga ttcactcaga ttgtctggga aaagactaaa ggaacaggaa     540
gaaatcagta gcaaaaatcc tgctagatca ccagtaactg aaataagaac tcaccttta      600 agtcttaaat ctgaacttcc agattctcca gaaccagtta cagaaattaa tgaagacagt    660
gtattaattc caccaactgc ccaaccagaa aaaggtgttg atacattcct aagaagacct    720
aatttcacca gggcgactac agttcccttta cagactctat cagatagcgg tagtagtcag    780 cacccttgaac acattcctcc taaaggtagc agtgaactta ctactcacga cctaaaaaac    840
attagattta cttcacctgt aagtttggag gcacaaggca aaaaaatgac tgtctctaca    900
gataacctcc ttgtaaataa agctataagt aaaagtggcc aactgcccac aagttctaat    960
ttagaggcaa atatttcatg ttctctaaat gaactcacct acaataactt accagcaaat   1020
gaaaaccaaa acttaaaaga acaaaatcaa acagagaaat ctttaaaatc tcccagtgac   1080
actcttgatg gcaggaatga aaatcttcag gaaagtgaga ttctaagtca acctaagagt   1140
cttagcctgg aagcaacctc tcctctttct gcagaaaaac attcttgcac agtgcctgaa   1200
ggccttctgt ttcctgcaga atattatgtt agaacaacac gaagcatgtc caattgccag   1260
aggaaagtag ccgtggaggc tgtcattcag agtcatttgg atgtcaagaa aaaagggttt   1320
```

```
aaaaataaaa ataaggatgc aagtaaaaat ttaaaccttt ccaatgagga aactgaccaa      1380
agtgaaatta ggatgtctgg cacatgcaca ggacaaccaa gttcaagaac ctctcagaaa      1440
cttctctcat taactaaagt cagctctccc gctgggccca ctgaagataa tgacttgtct      1500
aggaaggcag ttgcccaagc acctggtaga agatacacag gaaaaagaaa atcagcctgc      1560
accccagcat cagatcattg tgaaccactt ttgccaactt ctagcctgtc gattgttaac      1620
aggtccaagg aagaagtcac ctcacacaaa tatcagcacg aaaaattatt tattcaagtg      1680
aaagggaaga aagtcgtca tcaaaaagag gattccottt cttggagtaa tagtgcttat      1740
ttatccttgg atgatgatgc tttcacggct ccatttcata gggatggaat gctgagttta      1800
aagcaactac tgtcttttct cagtatcaca gactttcagt tacctgatga agactttgga      1860
cctcttaagc ttgaaaaagt gaagtcctgc tcagaaaaac cagtggagcc ctttgagtca      1920
aaaatgtttg gagagagaca tcttaaagag ggaagctgta ttttttccaga ggaactgagt      1980 cctaaacgca tggatacaga aatggaggac ttagaagagg accttattgt tctaccagga      2040
aaatcacatc ccaaaaggcc aaactcgcaa agccagcata caaagacggg cctttcttca      2100
tccatattac tttatactcc tttaaatacg gttgcgcctg atgataatga caggcctacc      2160
acagacatgt gttcacctgc tttccccatc ttaggtacta ctccagcctt tggccctcaa      2220
ggctcctatg aaaaagcatc tacagaagtt gctggacgaa cttgctgcac accccaactt      2280
gctcatttga aagactcagt ctgtcttgcc agtgatacta acaattcga cagttcaggc      2340 agcccagcaa aaccacatac caccctgcaa gtgtcaggca ggcaaggaca acctacctgt      2400
gactgtgact ctgtcccgcc aggaacacct ccacccattg agtcattcac ttttaaagaa      2460
aatcagctct gtagaaacac atgccaggag ctgcataaac attccgtcga acagactgaa      2520
acagcagagc ttcctgcttc tgatagcata aacccaggca acctacaatt ggtttcagag      2580
ttaaagaatc cttcaggttc ctgttccgta gatgtgagtg ccatgttttg ggaaagagcc      2640
ggttgtaaag agccatgtat cataactgct tgcgaagatg tagtttctct ttggaaagct      2700
ctggatgctt ggcagtggga aaaactttat acctggcact tcgcagaggt tccagtatta      2760
cagatagttc cagtgcctga tgtgtataat ctcgtgtgtg tagctttggg aaatttggaa      2820
atcagagaga tcagggcatt gttttgttcc tctgatgatg aaagtgaaaa gcaagtacta      2880
ctgaagtctg gaaatataaa agctgtgctt ggcctgacaa agaggaggct agttagtagc      2940
agtgggaccc tttctgatca acaagtagaa gtcatgacgt ttgcagaaga tggaggaggc      3000
aaagaaaacc aatttttgat gccccctgag gagactatac taactttgc tgaggtccaa      3060 gggatgcaag aagctctgct tggtactact attatgaaca acattgttat ttggaattta      3120
aaaactggtc aactcctgaa aaagatgcac attgatgatt cttaccaagc ttcagtctgt      3180
cacaaagcct attctgaaat ggggcttctc tttattgtcc tgagtcatcc ctgtgccaaa      3240
gagagtgagt cgttgcgaag ccctgtgttt cagctcattg tgattaaccc taagacgact      3300
ctcagcgtgg gtgtgatgct gtactgtctt cctccagggc aggctggcag gttcctggaa      3360
ggtgacgtga agatcactg tgcagcagca atcttgactt ctggaacaat gccatttgg      3420 gacttacttc tcggtcagtg tactgccctc ctcccacctg tctctgacca acattggtct      3480
tttgtgaaat ggtcgggtac agactctcat ttgctggctg gacaaaaaga tggaaatata      3540
tttgtatacc actattcata a                                                3561
```

<210> SEQ ID NO 8
<211> LENGTH: 38196

<212> TYPE: DNA
<213> ORGANISM: Homo sapiens

<400> SEQUENCE: 8

| | | | | | |
|---|---|---|---|---|---|
| gcaggccgaa | tggtggattt | aattggccgg | agtttagggc | gcgcttggcc | cgcgtgggtc | 60 |
| agctgatcgc | gcactgaggg | tgcgatcccg | ggctccccat | tccttcctgg | ggcgcctccc | 120 |
| cggcccaggg | ccaactgggt | cccggtgtcg | gcaggcctgg | ggtcggcgac | ggctgctctt | 180 |
| ttcgttctgt | cgcctgcccg | atggacgagc | ctcccgggaa | gccctcagc | tgtgaggaga | 240 |
| aggaaaaggt | gccggggtg | cgggaagggc | ggacgcagga | ctctgacccc | gctttcccag | 300 |
| ggttttaggc | ctggctttgt | gtcctcggca | gtccgagggc | agcagtatca | tctgaccacc | 360 |
| ccctcctctt | agggctgagg | gggcacagaa | aatgaaaatg | tggaaatagc | gtggtgctca | 420 |
| cgtggtggcg | tttaaagaac | aaatttcatt | acagtagcag | cgcattaata | caatgtgtaa | 480 |
| cagtttgtag | ataaagctgt | atcgacaccc | ttgctcctcc | ccctcccac | accctcaatc | 540 |
| tttacttctc | ccccggacg | gcctcaagta | aatcttttaa | gtctggtact | tccaggtcct | 600 |
| ttcgtgtgtt | aatgtgggtg | gtggaggagg | ggcgtatccc | taaccaccaa | aaaggaatcc | 660 |
| tatgtatatt | ttttggagaa | gggaatgttc | ataaatggta | tgatctgaat | ggttctgcag | 720 |
| gttccgttta | gctttcctgt | caggacatgt | ttatctacct | tgctttcttt | tttaagttct | 780 |
| agacagtatg | ttgtagtttg | gaagtgccct | cgttttgttt | ctttttttctt | cctttttctgt | 840 |
| ttttcttctt | ttttgagaca | gagtctcact | ctgccaccca | tgctggggtg | cagtggcgcg | 900 |
| atctcggctc | actgcaacct | ccgcttcctg | ggatcaagcg | actctcctgc | ctcagcctcc | 960 |
| cgagtagctg | ggattacacg | aacccgccac | tgcacctggc | cttggaagtg | cccttgcttc | 1020 |
| tttagactgt | actttactga | tagacttta | ggatgtttcc | agcttgtgct | gatgttattc | 1080 |
| ttatcctggc | ttaccttctg | gtggaggtga | gaaagatcat | ttataagtaa | acaagataat | 1140 |
| ccccagacat | tgataagatt | ggtgggaggc | cagtctccct | ggctcacgcc | tgtaatcccc | 1200 |
| gcactttggg | aggccgagat | gggcagatcg | cttgagctca | gagtttgaga | ccagcctagg | 1260 |
| caacgtagtg | aaaccccgtc | tctactaaaa | atacaaaaat | tagccgggtg | tggtgacgcc | 1320 |
| agcctgtagt | cccagaggct | caggcctcag | aggctgatgc | acgagaatcg | cttgaaccag | 1380 |
| gggacgctga | ggttgcaggg | agctgccgag | atcgcgccac | tgcacgccag | gctggacgac | 1440 |
| agagtgagac | tgtctctcaa | aaaaaagaa | aattccttac | ggttggcaac | ttgtctagta | 1500 |
| gcatgttttg | cacataggtt | ttgttttgtt | tgtttttgag | acagactctc | cgctctatct | 1560 |
| cccaggctgg | agtgcagtgg | ctcgatcttg | gctcactgca | acctccgcct | tcaggttca | 1620 |
| agcgattctc | ctgcctcagc | ctcccgagta | gttgggatta | cagacgccca | acaccacgcc | 1680 |
| gggctaattt | ttgtattttt | agtagagaca | gggtttctcc | atgttggcca | ggctggtttt | 1740 |
| gaactcctga | cctcaggtaa | tctgcccgcc | ttggccttcc | aaagtgctgg | gattacaggt | 1800 |
| gtgagccact | gcaccggcc | ttttttttt | tttttttttt | caagcagagt | ctcgctctgt | 1860 |
| tgcccaggct | ggagtgcagt | ggcgtgatct | aggcccactg | caacctccgc | ctccgggttc | 1920 |
| aagcaattct | cctgcttcag | cctcctacag | gcacccacca | ccacacccgg | ctcattttg | 1980 |
| tatctttagt | agaagcagga | tttccacatg | ttggccaggg | ggtctcgaa | ctcttgacct | 2040 |
| caaatgatcc | acccacctca | gcttccccaa | gtgttgggat | tacaggcgtg | agccactgcg | 2100 |
| cccagctgag | taggtctttt | cttttttta | aaaaggcat | gtatggagga | tggaaatctt | 2160 |
| gatgttttgt | tggttgaaag | atgagtacag | ctaaaaagtt | gctaaaaagc | agaaaaaccg | 2220 |

```
aggctggctt tgctgctgag agaatccttt gaagcaaaga agccagagag acgagggaat    2280
ctaggctttc agagaacagt aatttgattc agcccaattc atttatttat ttaataaata    2340
tttgttaaat gcctactgtg tgcctggctg agattgagc aatgatagct ccaacctcac     2400
tggccttctg cgtgttcctc aaacgtaggt aacctattcc actgcagagc ttttatattt    2460
gtggttccct ctgcctgggg taccgttccc tctgatcttc ccaaaactag ctccttcctc    2520
attcagtctt aggctcaaat gatagtcaaa aatgcctccc tgaccactgt aactaaagta    2580
gtccctgtca gtaggccagt aactctctca tatcactctg tttatctgtg tatttttta    2640 ccttgtaaaa tcatttctgt ttgttttctt atttattatc tgtctccctc actgtatgta    2700
aattgcatct agaatagcat ctggagcact aattgacaca tagtgggtat caattattat    2760
tccaggtact agagatacct ggaccattaa cggataaata gaagattcat tgttgagtg     2820 actgaggatg gcagttcctg ctaccttcaa ggatctggat gatggggaga aacagagaac    2880
atagtgtgag aatactgtgg taaggaaagt acagaggact ggtagagtgt ctaacctaga    2940
tttggagaag gacctagaag tctatcccag ggaaataaaa atctaagcta aggtttgagg    3000
aatcagtagg aattggcaaa ggaaggacat gttccagatg ataggaacag gttatgcaaa    3060
gatcctgaaa tggtcagagc ttggtgcttt ttgagaacca aaagtagatt gttatggacc    3120
agtgctactc cctgcctctt gccaagggac cccgccaagc actgcatccc ttccctctga    3180
ctccaccttt ccacttgccc agtattgttg gtgttttct tcttccagtt aaaggagaaa     3240
ttagcattct tgaaaaggga atacagcaag acactagccc gccttcaggt aagtgaatcg    3300
tattctcaaa ttaaggtgtt atagtacaaa caatttaaaa acagttcttg actctataaa    3360
actttaaaga aaacgtattt ctggggctgt ttttgtctcc tctagcgtgc ccaaagagct    3420
gaaaagatta agcattctat taagaaaaca gtagaagaac aagattgttt gtctcagcag    3480
gatctctcac cgcagctaaa acactcaggt aaatctagac cattcactta tgcctgcttt    3540
attattcatt tcccaggtat attttggcta ttgttctttt tcccacagtg tgaagataat    3600
gactagcaat agacgcttta attttaattt taattttaat tttattttt tgagacagag     3660 tctcactctt tgttacccag gctggagtgc agtggcacaa tcttggctca ctacaacctc    3720
caactcccag gctcaagtga ttctcgtgcc tcagcctcct gagtagctgg gactacaggc    3780
acgtgcacta ccacacctga ctaattgtta tattttagt agagatgggg tttcgccatg     3840
ttggccaggc cggtcttgaa cccctggctt caaatgatct gtctgcctgg gcctcccaaa    3900
gtgctgggat acaggtgtga gccactgtgc ccggctgcaa tatattctaa ttaacataaa    3960
attcatatgc cgtaaaatct atagtctcta ttttcagtta gactgtttat tctttttccc    4020
tctcttgctc ttttccctc tcaattttca gaaattatat ttattgttta aatattagaa     4080
aggttttttg ttttgttttg ttttattttt gagacagagt ctcactctgt catcaaggct    4140
ggagtacagt ggctcaatca cagctcactg cagcctccac ctcctgggtt caagcaattc    4200
tcctgcctca gcctcccgag tacctgggac tacaggcgca caccgccacg cccagctaat    4260
ttttgtattt ttagtagaga cagggtttca ccatgttggc caggatggtc ttgatctcct    4320
gaccttgaga tctgcctgcc tcagcctccc aaagtgctgg gattacaggt gtgagccacc    4380
gtgcccagtg aaaggttttt tttaaaaatg taagtatata tgaacagaga aaaattctag    4440
gtgaaaatat tctaaaaaca atgatcaatt ctgatgttta cattcaagta atttataatc    4500
ataaaactga ggggttattg aaatgggagt gttattaaaa ttacttgagc caaggggaa     4560 aataaagaaa gaaatacatg agatagaaaa ctagttgaga tttagaagtt aagagaagag    4620
```

```
attgtgtgat aaagaatact ctgttcgttt aaaaaacatt tttagcacaa tgctgtttgt    4680
ttatatgtac ttaaaatttc atagattatt agaatttaaa aaatcagaac ttttaaaaat    4740
atgtacagta tggagtatgt acagttcctt tacatactcc atcagatagt agaagtagtc    4800
aacaccttga acacattcct cctaaaggta acagtgacct tactactcac agcctaaaaa    4860
ataggtttat ttcacctgta aattcatctg cctgaatgaa atgtcactga ttctttctta    4920
aataaatgtt tagtagtatt tatatataat aggttaaaaa tgagtatttt ttgttttatt    4980
ttataagaaa aatataagtt atatacattt ttttcctcct cagaacctaa aaataaaata    5040
tgtgtttatg acaagttaca catcaaaacc catcttgatg aagaaactgg agaaaagaca    5100
tctatcacac ttgatgttgg gcctgagtcc tttaaccctg gagatggccc aggaggatta    5160
cctatacaaa gaacagatga cacccaagaa catttttcccc acagggtcag tgaccctagt    5220
ggtgagcaaa agcagaagct gccaagcaga agaaagaagc agcagaagag gacatttatt    5280
tcacaggaga gagactgtgt ctttggcact gattcactca gattgtctgg aaaagacta    5340 aaggaacagg aagaaatcag tagcaaaaat cctgctagat caccagtaac tgaaataaga    5400
actcaccttt taagtcttaa atctgaactt ccagattctc cagaaccagt tacagaaatt    5460
aatgaagaca gtgtattaat tccaccaact gcccaaccag aaaaaggtgt tgatacattc    5520
ctaagaagac ctaatttcac cagggcgact acagttcctt tacagactct atcagatagc    5580
ggtagtagtc agcaccttga acacattcct cctaaaggta gcagtgaact tactactcac    5640
gacctaaaaa acattagatt tacttcacct gtaagtttgg aggcacaagg caaaaaaatg    5700
actgtctcta cagataacct ccttgtaaat aaagctataa gtaaaagtgg ccaactgccc    5760
acaagttcta atttagaggc aaatatttca tgttctctaa atgaactcac ctacaataac    5820
ttaccagcaa atgaaaacca aaacttaaaa gaacaaaatc aaacagagaa atctttaaaa    5880
tctcccagtg acactcttga tggcaggaat gaaaatctto aggaaagtga gattctaagt    5940
caacctaaga gtcttagcct ggaagcaacc tctcctcttt ctgcagaaaa acattcttgc    6000
acagtgcctg aaggccttct gtttcctgca gaatattatg ttagaacaac acgaagcatg    6060
tccaattgcc agaggaaagt agccgtggag gctgtcattc agagtcattt ggatgtcaag    6120
aaaaaagggt ttaaaaataa aaataaggat gcaagtaaaa atttaaacct ttccaatgag    6180
gaaactgacc aaagtgaaat taggatgtct ggcacatgca caggacaacc aagttcaaga    6240
acctctcaga aacttctctc attaactaaa gtcagctctc ccgctgggcc cactgaagat    6300
aatgacttgt ctaggaaggc agttgcccaa gcacctggta agatacac aggaaaaaga    6360 aaatcagcct gcacccagc atcagatcat tgtgaaccac ttttgccaac ttctagcctg    6420
tcgattgtta acaggtccaa ggaagaagtc acctcacaca aatatcagca cgaaaaatta    6480
tttattcaag tgaaaggtaa atcaagatgt gtttgatgat gatgatgatg atgatgaaag    6540
ttaacaatta ctatttgcct ggcacttcct tttctttctt ttctaaaaag tgacagggcc    6600
aagtgtggtg gcttacgtct gtaatcccag cactttggga ggctgaggaa cagagtgaga    6660
ccctggctca aaaaaattta aataaataaa taaataaata aataaataaa taataaaaaa    6720
taaagagaca ggggctcact gttgtccagg ctggagtgcc gtggtgcagc ctctatctcc    6780
tgggctcaaa tgttcctcct gcctcagcct cccaactagc tgggactact ggcatgtacc    6840
accatgcctg gctaatgttt taaattttt tgtagaggtg aggtcctgcc ctgttgccca    6900
ggctgatctt gaactcctgg cctcaaacaa tcctcccacc acagcctctc aaagtgctgg    6960
```

```
gattacagac gtgagccact gtgtccagct tgcctggcac tttctaaatg ttgtacagat    7020
actaactcat tgaatcatca cagcagtcct atgtgaggta gaatctattt tcattctcac    7080
tttacaggtg aggaaactaa agtacaggga gattaaaata actttactta atttaattaa    7140
aatcacagag ccaggattca aacctggcgg tatggtgcca gagttcacta atagagctga    7200
aacaattcaa cactgaaaag gaaaatgtat tggttgttta cgtaatatta catattcagg    7260
ttcaatacaa ttctttgggt agaagcttca cagctaacat agaaagtgtt tttgaagtaa    7320
aatggaatgt gtactagagg aagactctat gttgggcttg gtggctcacc cctgtaatcc    7380
cagcacttcg ggaggccaag gtgggaggat tgcttgagcc caggagtttg agaccagctt    7440
gggtaaaatg atgaaacccc atctctacaa aaaaaaatat agaaaaatta gccaggtgtg    7500
gtggtatatg cctgtggttt cagctacttg agaggctgag gtgggaggat cacttgagct    7560
caggaggttg aggctgcggt gagctgtgat tgcaccactg cactccagtc tgggtgatag    7620
agcaaaaccc tctctcaaaa aaaacaaga ctaagactcc actgactatc tcttttagaa    7680
gtcatcatgt aatgaaaagg cctaagcaac ttttttggat aaaatatcta atgcagtgtc    7740
tctaaggcct ccaagggaca cagaattttg gaggatgggc agcaacgata cattgtaatt    7800
taaactttca attcatttac tgagaattta atcatatctg atgaactaag cacaaaatct    7860
gggtaattca ttgtggctct aaactaggga tcagcatact ttctagaatg gccagatag    7920 cacagatttt agtctttgtg ttctgtctgt ctcaactact cagctatgtg ccagagcagc    7980
cagtcaactt gtaactgtga ctgtgttcca acgcaccttt atatgcactt tacagccaag    8040
ttcctaaaac aaaaaaacaa ctttatgtgc aaaaataggt agcaggctgc tctgtaccat    8100
tggacatgga cttggtctat aagctgtgac taattaatcc aaaaataata attgtgactt    8160
ttcatcatct tttaagcgaa caaggataca aagtcatcaa aaagtaggca atccagtaat    8220
ctagaaatac tgttttttac acagtagttt ttttttattg ttgttgagac agtttcaccc    8280
ttgtcgcccc ggatagggtg cagtggcgct atctcagctc actgcaacct ctgcctccca    8340
ggttcaagcg attctcccac ctcagccccc tgagtagctg agattacagg tgcccaccac    8400
cacacccagc taatttttat atttttcagta gagatgggtt tttgccatgt tggccaggct    8460
ggtctctatc tcctgacctc aggtgatcta cccacctcgg cctcccaaag tgctgggatt    8520
acaggcgtga gccaccaggc ccagccagta gtttgaaata gtctgctata attgtagtaa    8580
actgcagcta catttaaaaa ctttttttct caaggtgaca ttcacgtaac aaaattaacc    8640
atttaaaatt aagtgaacaa gtcaatacat ttacagtgtt gtgcaaccac caccttatct    8700
cattctaaaa catttcatc accccctaaac cccatacccca ttaagcagct gctacccatt    8760
tcctcccctg accccctact tcatccctgg gcaaccacca atctgcattc tatctctatg    8820
gatttacctg ttctgggtat ttcatatata tggaatcata caatatgtga cctttttgtgt    8880 ctggctgctc agcataatgg gtttgtttgt ttttgagatg gagtgtcact ctgttgccca    8940
ggctggagtg cagtggcaca atcttggttc actgcaacct ctgcctccca ggttcaagtg    9000
attctcctgc ctcaacctcc tgagtagctg agattacagg cgcctgccac catgcctggg    9060
taatttttgt atttttagta gagacggggt ttcaccatgt tgtccaggct ggcctcaaac    9120
tcctgacctc aagtgatcca cctgccttca gcctctcaaa gtgatgggat tataggtgtg    9180
agccactgag cctggccact tagcataatg ttttttaaggt atgtttctgt tgtaacatgc    9240
atcagtactt tgttcctctt tatggctgac tagtattcca ttgtatgtat ataccacagt    9300
ttgtttatgc attcatcatt gaggatatag caacattttg aatgatgtgg gataccattt    9360
```

```
gcaataagag cggtaaattg ctactcagga ggctgatgtg ggaggattgc ttgagcctgg    9420
gaggcagagg ttgcagtgag ccaagatctc gccactgcac tccagcctgg gcaacagagt    9480
gagacctcgt cttgaaacaa acaagcaaac aaaaagcagt aaattactct ttgcttcaaa    9540
aggggactaa gttttccata gtgagaagag ccagcatttt gtagaacata ctctggcagc    9600
ctgttgaaat cacagtttta gaggtaggaa agaatgtagg tattttttagt tcatttccct    9660 tatgagagac aatgagaaaa gggaaaatga aataaatcga tttgcctaag gtttcactgc    9720
aaatcagtgg ttgagttgag acttgtcctc agtcccttct cctagttaat actattgacc    9780
atacactgtt ttgttttgtt tggttttatt tatttatgta tttatttatt tatactgttg    9840
gccatacact gttttgtttg gtttggtttt atttatttat ttattttttg agacagaatc    9900
tcgctctgtt gcccaggctg gagtgcagtg gtgcagtttc agcccactgc aacctctgcc    9960
tcccgggttc aagtgattct cctacctcag cttcctgagt agctgagatc acaggcacgc   10020
accaccatgc ccagctaatt tttttagttt agttttttt ttttttttt tttttttga    10080 gacagagtct cactctgtcg cccaggctgg agtgcagtgg tgccatctcc gctaactgca   10140
agctccgcct cctgggttca cgccattctc ccacctcagc ctccggagta gctgggacta   10200
caggcgccag ccaccacacc cggctaattt ttttttttt ttttttttgt attttttagta   10260 gagacggggt ttcaccatgt tggccaggct ggtcttgaac tcctgacctc aagtgatccg   10320
cctgcctcag cctctgaaag tgctgagact acaagtgtga ggcaccatgc ctggccttat   10380
tttttttaat ttttatttat ttatttattg tttttaaaga cagtctcact gtgttgccca   10440
ggctggtctg gaactcctgg gctcaagcaa ttctcttacc ttgacctctg aaagtactag   10500
gattacagct gtgagctacc atacctggct agcaatacac tgttttgggt agtgcagaaa   10560
aatagctgct aattaatcaa ctaactcatg accgttgttt gaacccttcg cccaagtttc   10620
tgagtcatgg atgggaaaag taatgaacat ttttagtat atttgagttt agaagctcac   10680
tctttgttgg gtattacatt taagaatggt ttaacatgtt tctttgatag gacttcattg   10740
taaacattaa gttcattctg gggaaattaa ggttcattaa aatgtttctt ttaaatctag   10800
gagatcctat tctctttgtc atcagtgaaa cagattgtct gttttgttgg gttttgttac   10860 tatttttgtga cttattttc ttctttaggg aagaaaagtc gtcatcaaaa agaggattcc   10920
ctttcttgga gtaatagtgc ttatttatcc ttggatgatg atgctttcac ggctccattt   10980
catagggatg gaatgctgag tttaaagcaa ctactgtctt ttctcagtat cacagacttt   11040
cagttacctg atgaagactt tggacctctt aagcttgaaa aagtgaagtc ctgctcagaa   11100
aaaccagtgg agccctttga gtcaaaaatg tttggagaga gacatcttaa agagggaagc   11160
tgtatttttc cagaggaact gagtcctaaa cgcatggata cagaaatgga ggacttagaa   11220
gaggacctta ttgttctacc aggaaaatca catcccaaaa ggccaaactc gcaaagccag   11280
catacaaaga cgggcctttc ttcatccata ttactttata ctcctttaaa tacgttgcg    11340 cctgatgata atgacaggcc taccacagac atgtgttcac ctgctttccc catcttaggt   11400
actactccag cctttggccc tcaaggctcc tatgaaaaag catctacaga agttgctgga   11460
cgaacttgct gcacacccca acttgctcat ttgaaagact cagtctgtct tgccagtgat   11520
actaaacaat tcgacagttc aggcagccca gcaaaaccac ataccaccct gcaagtgtca   11580
ggcaggcaag gacaacctac ctgtgactgt gactctgtcc cgccaggaac acctccaccc   11640
attgagtcat tcacttttaa agaaaatcag ctctgtagaa acacatgcca ggagctgcat   11700
```

```
aaacattccg tcgaacaggt acaatccatt tcctctgtga aattttctct gaaggaatga   11760
aatgccttag tgaatgtaaa cagcatgact tgcttgcgca ttgggccttc cacgtttaag   11820
aatggtttga cgtgtttctt tgatatgatt tcattgtaat cattaagttc attctgggga   11880
aattaaggtt cattaaaatg tttcttttaa atatgggagg tcctattctc tttgttatca   11940
gtgaaacagt ttgcatttgg agctttgctg ctgttataag aggaaataaa gacaatacga   12000
agtagacatt tgatgagtg ggtaatgcag gcagacatta tacataaagt gtagactaat   12060
gatgtgactt ttgttttcac agactgaaac agcagagctt cctgcttctg atagcataaa   12120
cccaggcaac ctacaattgg tttcagagtt aaaggtcaga agaatattct cttccagtgt   12180
ctcgtgtctt acatatgaaa actttaatga actgaaaaga attcagtcat atagcttctt   12240
gttctttaat actattaaag atattggtaa acagattcag aaaaacagat ttggattggt   12300 tattttccc aatatttacc tctgtttatg ttttgagctc tcctcttaaa gtttctatgc   12360
caacctattg gcaagaacaa cttaggctaa gtaactgaac ttcatgtcta aatctaagtt   12420
agggagctgg gcacggtggc tcaccccta atctcagca ctttgggagg ctgaagcggg    12480
ctgatcactt gaggtcagat gtttgaggcc agcctggcca acatgatgaa accccatctc   12540
tactaaaaat acaaaaatta gccgggcgtg gtggtgggcg cctataatcc cagctgctag   12600
ggaggctgag ggaagagaat acttgaactg ggagacagac gttgcagtga gccaagatct   12660
taccactgca ctccagcctg ggcgagtgag actctgtctc aaaataaaa taaataaat    12720 ctaacaggca tttgacgga gtgaaatgag agttattcat gcctctccta ctcaaatggt   12780
gtaatgtttc tggaagaatc acttatgtg atttataaga aatgggag cagttctagt      12840 ggttaatctt ttctgtgcag tgtggtaact gaaaatgttg cattactaaa tgtcctaggt   12900
gtagggttga agatggggt gcagaagctc tcccagagaa tcactggtgt gaaggaaaac    12960
acttcaaatc cacataaagt ttttcccagt tactggctat gtcaccttgg acaaattgtg   13020
taacctctga gccccagatt cctttctat aaaggatgca tagtaatacc tatgctctgt    13080
ttcggaattt attcttgagt caattttaat aacttatttt attttttgag acagagtctg   13140
ttgcctaggc tggagtgcag tggggcaatc tccaatctcc aatctccact cactgcaacc   13200
tccgcctaca ggttcaagca attctcgtgc ctcaacctcc atagtagctg ggattacaag   13260
tgtgcgccac cacgccttgc taattttgt atttttagta gaaatggggt tttgccatgt    13320
tggccaggct ggtcttgaac tcctgacctc aggggatccg cctgccttgg cctcccaaag   13380
tgctgggatc acaggcatga gccaccatgc ccagtgtcct aataacttag tctcttaaag   13440
aatcaactat ttcattcata ttttcaaatg tgtaggtaaa aagttacttc ttatagatta   13500
ttaaaatctg tgtatatgta attaagcctc tcttccccat tctcccattt ctaaattatt   13560 gttttctac attagactcg agagttggcc attacgtggg tcttccaaac aaactagttt    13620
ttggttgtat tgattattaa ttgggttgtg ttttttgtt gttgttgttt ggttttctag    13680
ttcatttatt tctgttttta taataaacag gataactgta aatcattcct tcctactttt   13740
ttttattgtt cttatttgt tcttgtactg acttcctgag ctgcatgctt acttgatttt   13800
aatctttctt gttttcttaa aaatgccttt gtgattatga ttttctttt tttttttttt   13860 ttttgagacg gagtcttgct ctgtcgccca ggctggactg cggactgcag tggcgcaatc   13920
tcggctcact gcaagctccg cttcccgggt tcacgccatt ctcctgcctc agcctcccga   13980
gtagctggga ctacaggcgc ccgccaccgc gcccagctaa ttttttgtat ttttagtaga   14040
gacggggttt caccttgtta gccaggatgg tctcgatctc ctgacctcat gatccacccg   14100
```

```
cctcggcctc ccaaagtgct gggattacag gcgtgagcca ccgcgcccgg ccgtgattat   14160
gattttcctt ggaaatttcc aaattttctt ggaaatactg ctttggccac gctctgtggt   14220
ttgatacata gtgctcccat ggtcataata gtagatagta taatgtatgt tgtttcaatg   14280
ttactccctc cgaggaataa cattgaaacc tgtggtttca gcccatgagt ggttcatcag   14340
gatgtttaat tttcaaatgg ataagttcta caggattttt tttgtggtta tatctgaatt   14400
tattccatct ggactataca ttttaaaatc tttcatgggc cgggcacggt ggctcatgcc   14460
tgtaacccca gcactttggg aggccgaggt gggtggatca cttgaggtca ggagttcaag   14520
accagcctgg ccaaatggtg aaaccttgtc tctactaaaa atacaaaaat tagctgggtg   14580
tggtggcggg cgcctgtaat cctagctact cggaaggctg aggcaggaga atcgcttgaa   14640
cccgggaggc gaaggttgca gtaagccgag attgcaccac tgcactccag cctgggtgat   14700
aaagtgagac tcagtcccaa aaacacccaa aaattaaaat taataaaata aataaaaaat   14760 aaaatcttc atgatgtaag tttgataggc atttttttag gtacataaga accacaaagc   14820
tctttctttt cacctgcata agacttaaat tttacatacc tactgtttca ttgaattata   14880
attcatcact ttgcatactt atgctttgca taaaacagca ctcgagtgcc actttaacag   14940
aactgttgcc attgtgtcag aatccttcag gttcctgttc cgtagatgtg agtgccatgt   15000
tttgggaaag agccggttgt aaagagccat gtatcataac tgcttgcgaa gatgtagttt   15060 ctcttttggaa agctctggat gcttggcagt gggaaaaact ttatacctgg cacttcgcag   15120
aggtaagtgg gaatctcgag ctgaaagaga tctttgcagc catttgcctg ataatgtaga   15180
tgggcagctt accaaaattg ggagctatga ccatgcaagg cagaacagag atgaggtttt   15240
tttcccaaca ttttattatg aaaagtttca aacatccaga aaagttgtat agtgagcacc   15300
catataccca ccattctaga ctctaccatt aacatcctgc tttgttcgct ttatcacaaa   15360 ttttttgtttg tttgtttgag acagggtctc actctgtcat gcaggctgga gtgcagtggc   15420
atgatcacgg ctcactgcag tttcaacctc cccaggctca gtaatcctct cacctcaccc   15480
tcccaagtag ctgggaccac aggcatgcac caccatgtct ggctaatttt ttattgtatt   15540 ttttcttct tctttttatt gagatggagt cctgctctgt cacccaggct ggagtgcagt   15600
ggcatgatct cggctcactg tcaacctctg ccgcccaggt tcaagggatt cttgtgcctc   15660
agcctcctga gtagctggga ttacaggtgc ccaccaccat gctggctaa ttttttttgta   15720 tttttagtag agacgggatt ttgccatgtt gcccaggctg ttcttgaact cctgacctca   15780
ggcaatccgc ctgcctcagc ctcgcaaagt gctgggatta caggtgtgag ctaccacacc   15840
tggcctatat ttttatgca gacagggttt tgccatgtcg cctgggctgg tcttgaactc   15900
ctgggcttaa gccatccgcc tgcctcagcc tcccagagtc tgggattaca ggtgtgaa   15960 ccaccatgcc cagcccatca caggtttatc tagatatggg ttttttgttt gtttgtttgt   16020
ttttggagag agagtcatac tctgttgccc aggctggagt gcagtgggc gatcttggct   16080 tactgcaatc tccgcttccc gggttcaagc aattctcctg cctcagcctc ccgagtagct   16140
gggactacag gcgcccacca ccacgcccag ctaattttg tatttcagt agagatgggg   16200 ttttaccatg ttggccagga tggtctctaa ctcctgacct caagtgatcc actcgcctcg   16260
gcttcccaaa gtgctggggt tacaggcatg agctctacac ccagcctaga gacgggtttt   16320
tacactagac ctgttggagg agcttagaat tttatgtcta ttctgacttt gacacttgct   16380
gatatttgta ctccttgccc ttcaccaagg cattattttg cttcttttct acatgtattt   16440
```

```
ccttctggtc ttttcccacc atcatataca tcttacaagc ttgcaatctt agtgtgctta    16500 aaattttag atctgtcttt tctcaccata catataaaca tttttctggc caggcgaggt     16560
ggctcacgcc tgtaatccca acactttgag aggctgaggt gggtggatca cctgaggtca    16620
ggagttcaag accagcctga ccaacatggt gaaacccgt ctctcctaaa aataaaatta     16680
gccaggtgtg gtggcgaatg cctgtaatcc cagctactca ggaggctgag gcaggagaat    16740
cgcttgaacc caggaggtgg aagttgcaat gagctgagat tgtgccattg cactcaaggc    16800
tgggcaacaa gagtgaaact ccgactcaaa aaaaaaatt tccttgttcc tgtagagtct     16860
tcatacttga atatacctca ttcttgctct ccaaatatat acaacatcta acactgtgct    16920
ttacacagag gtgcccaata aatatttgtt cagtgaacat agatatactt ttaaatggct    16980
gcataaatat tctttacatt cacatgccaa aatatcccca attattcccc tattgttaga    17040
attataccct gcattaggta aatgctcagt aagcactatt atgctattat gcatatagtt    17100
tatttagatt tacagctaat aaaagagtt ttctgagcct tcaaatgatg aaaattatcc     17160
ttgtacagtg agaatacaaa agaatgtgat aaattttgga aaatctggat taaacaaaaa    17220
tgaaacaacc aagcataatt tttggctgct ttgttttatt taggttccag tattacagat    17280
agttccagtg cctgatgtgt ataatctcgt gtgtgtagct ttgggaaatt tggaaatcag    17340
agagatcagg tatgtaattc ccaaggagtg atttgttttt ccttcatctt tgtctctgtc    17400 agctgggtttt aagtgcaggt aataacctag gcttgagtct tgaaagaatc tgaaagatct   17460
aaagagagag agatttgttt aaaaaaaaat caatagaatg acatccctga ctgaagtttc    17520
tatttaaaat gtgaacctag gctgggcgca gtggctcacg cctgtaatcc cagcactttg    17580
ggaggccaag gaaggtggat caactgaggt caggagtttg agaccagcct ggccaacatg    17640
gtgaaactgt gtctctactg aaaatacaaa aattagcctg gtgtatagca cctgcgggtg    17700
cctataatcc cagctactca ggaggctgag gcaggagaat tgcctgaacc cgggaaacag    17760
aggttgcagt gagctaagat cgtgccacca ctgcattcct tctggatgac agagtgagac    17820
tttgtctcaa aaaaaaaaa aaaaaaaaa aaaaaggcc gggtatggtg gctcacacct       17880
gtaatcccag cactttggga ggccgaggca ggtggatcac gaggtcagga gttcgagacc    17940
agcctgacca acatggtgaa accccgtctc tacaaaaata cagaaaaatt agccaggtgt    18000
ggtggtgcgc acctataatc ccagctactc aggaggctga gcaggacag tcgcttgaac     18060 ctgggaggca gagttgcagt gagccaagat tgtgccactg cactccagcc taggcgacag    18120
agcaagactc tgtctcaaaa aaaaaaaaaa aaaaaagtg aacctagtcc tttaatatta    18180
aaaggttact cctcacatca ccccattttt ccttatattt ggcttagggc attgttttgt    18240
tcctctgatg atgaaagtga aaagcaagta ctactgaagt ctggaaatat aaaagctgtg    18300
cttggcctga caaagaggag gctagttagt agcagtggga ccctttctga tcaacaagta    18360
gaagtcatga cgtttgcaga agatggaggg taagaaaagc attgattgat ttttaactat    18420
tagatgaaga atgattttat cacaggtttc agagaaagtt gggtaactag gatctcgttt    18480
ttctgtgctg ggggtgtaat ataagcatgt accgcatcaa cactaggtta tgacatagaa    18540
gcaggttagt gaggtggaag ccagacatgt caggatgaa gtcaaagaag gtgagaggct      18600
cagcaaatgt agtttgttct tcagtcttct tgaaatctgt gtgtccctta aatgttagaa    18660
atacctctgc tgggcacagt ggctcatgcc cataatccca gccctttggg aggccaaggc    18720
agaagtttga gcccaggagt tcaagaccag ttggggccac atagcagggc cccatctta     18780 caaaaaattt aaaaattagc tgggtgtggc agagcatgcc ttgtggtccc agctactagg    18840
```

```
gagtctgagg tggaaggatc acttgagctc aggagttcaa gggtgcagtg agctgtgatc    18900
acgccaccac actccatctt gggcagcaga gcgagaccta atcttaaaca cacacacaca    18960
cacacacaca aatattttta aaatataga aataccttaa ggtcctagac cctttcctcg     19020
ttccacacac ttgtgtccat tgcttcactg accatcttgg tgctgactac ttgcaaacat    19080
acatttctac ctctgagctc tttcttgagc tctagacctg caggcctatt tattagacgt    19140
attggggaca ccttaaattc aaaatgttgc aaactgaact tacagcatct tctctattat    19200
atactcatta cactttattt ttattttca attacatttc attgttatta ttcatgtatc     19260
ttctaaaaat ggagggcagg gaactttggc ttatttattc atgatctgtt gcagtaatct    19320
aggcaagaga tgataattgt ttgcttaaat taggggtatg ttagtggaga tgggaagaag    19380
cagacagatt tctgagagat gagaagataa aattactggg acttggtgat tgactagatt    19440
gagaggaagg agagaatatc aacatggtag ggttggtcac ttgagtggtg accaagctcg    19500
aaatgtgggt attatccttg tctccttccc cccagtctag gtggtcactt gagtggtgac    19560
caaccctgaa acttggacat tagatggtga tgcaattcat tgagatagga atgcagaaag    19620
aaacaaaagg tttatagaaa aagttaacaa gtttaatttt gaatataatg aattcgaggt    19680
gcttgcagca tatctaggta gatattatga aagtaatata tgttcattgt agaaagttta    19740
gtatacacgt tttctgggtt agattttttt ttcctgatat taggttagtt tatattatgc    19800
agttcaacaa tgcggagaag ggctacctag agactgcttt agtgcaaagt actgacttt     19860 catactgttt taattacaga ggcaaagaaa accaattttt gatgcccct gaggagacta     19920 tactaacttt tgctgaggtc caagggatgc aagaagctct gcttggtact actattatga    19980
acaacattgt tatttggtaa gctttccctc taggtcctca gttccctcat ctgtagtatg    20040
aggatatacc tctaatttta cagggttgtt gtgaagatta aataagagag tatgtgtaaa    20100
catgattgtg gttttgtgtt gctgttgttg ttgttttgt tgtgttttga dacagagtct     20160
cctcctatca cccaggtggg agtacagtgg tatgatctcg gctcactgca acctctgcct    20220
cctggattca agtgattctc ctgcctcagc ctcccgagta gctgggatta taggcatgtg    20280
ccaccacacc cagctaattt ttgtatttt tagtagagat agggtttcat catgttggcc     20340
aggttggtct tgaactcctg gcctcaagtg atccacctgc ctcagactcc caaaatgcag    20400
ggattacagg agtgagccac cgtgcctggc taattttttgt atttttttagt agagaaggga   20460 ttttgccatg ttggctaggt tggtcttgaa ctcctggcct caagtgaact gcccgccttg    20520
gcctcccaaa ttgctgggat tacaggcatg agccactgcg cccggcctga ttgtggtttt    20580
tttgtcagat actatatact tgacttacca acaacatcat attaattgag acataaccaa    20640
aaaagatcag tctgagtaga ctatttaaaa ctaaatggaa ttctgttttc aaagatgtac    20700 acttcttct gcttttggtt agtggttgag tagtttctgt cagaccaact gtctaccttc     20760
gaataagtat acactctgga aaaaatacaa aaaacaactt tctaaaggca ccagagaaca    20820
agaaaaagaa gaaacatact ggaggggttt ctcccttag gtgaagggaa tggcactagg     20880
caacattcct attatggctt taagctaggg ggcaaggccc actctgctca ctgggtgact    20940
ggaagcctaa tagaagatct tctgtcccac tggcttagag aaccaaagga cagagttcag    21000
ggtgatcgca gctgctagaa agggagggga aaagtcctaa aaggagaga gcaaaaaata     21060 aaaaaaagaa ccctaaattc tagctataat gtttacctaa atatttgatt gacccttaa     21120 actgcatatt cataggtcag actgcttgga gtctggtaag actgaaagca gctcaggtaa    21180
```

```
gactgaaaga acgaatttca gtttcggcat ttggagttca agttcagcca agttaactgt  21240
ttactaggac agacaaactt acaaccaaaa aaatcagggc cgggcacggg tggctcatgc  21300
ctataatccc agcactttgg gaggccaagg caggcagatc acttgaggcc aagtgttcga  21360
gaccagcctg gccaacaagg caaaacccca gctctactaa aaatacaaaa attagccagg  21420
cgtggtggtg cacacctgta attccagcta ctcaggaggc tgaggtagga aatcgcttg   21480 aacccaggag gcggaggttg cagtgagtca agattgcgcc actgcactcc agcctgggcg  21540
acagagcaag attctgtctc aaaaaaaaat aataatttt taaaagtcaa tagaattgta   21600
ttttaaaagt acttaccata ttgtctggca cataggaggt attcagtaaa tgttaaaatt   21660
cctttttaaa aaatatttt aaaagaaaaa aacatcagtg tttgtcagag aacctaaca   21720 gaatacaaag tttttgcaac atattaatat cactgtaact aggatacagt ccaaagttac   21780
tcagtataca aaaataagt gtggcgtctc tactaaagat accccatctc tactaaagat   21840
acctcgtctc tactaaagac acaaaaatta gccaggcctg gtggtgcgag gctaaggcag   21900
gagaatcgct ggaacctagg aggcagaggt tgcagtgagc cgagatcgcg ccactgcact   21960
ctagcctgag tgacagagtg agactctgtc tcaaaaaaag aaaagaaaaa agtgtgatca   22020
caggaaccaa attaacagat tgtgatagg gaaaccatca caggagtccc cagccatctc   22080
ttttctgact atagggagaa ccatacccag ccacaggcac ttacttgcaa gtttaatttg   22140
tattaggaaa atagattgat gttttttctt ttctcagaag ccttgtctat taactgtttc   22200
cttagggcca gagtgggtct tggtaagagg aagttatatt agtgtgacca ctaccctagc   22260
tcttatgtac catccaaccc taaccttttt ttgttttctt tttttaaac actatggtga   22320 cttacaaccc taaccttcta ggaataaact agaaagtat ggcccttgag agaaacgttg   22380
tgcccttccc accagaaagc ctctgaaatt tgactatgtt ctgatctgcc agaagaccct   22440
gctttcagat gtcctgttgt ctagggtagc gcttggccac ttggagcact tcaccaggg   22500 tttctgccga ggggtgttat ttgaggatgg tgctcttcca gaagttgtct tttctattct   22560
ttgtgctatt tccatagtcc acaccttcat tatctgtctc ctgaactgtt aaaataatct   22620
agtagttcat ctccttgcca ttaatcaata ttcaaacttg atatttttt tttaaattt    22680 tttagactat gtcttactct gtcacccaaa ctagagtgca ctggcatgac catagctcac   22740
tgcaacctcg aatgcctggg ctcaaacgca ggtcattttt tattcgacta cattgtaaat   22800
actctttctt caactctacc ctcatccctc aaaagaaaac ctttacaggg gcccatgttt   22860
gctttccttc agcttttatt tccccggtgc tctagtacaa aaatgtcctc tccagctctg   22920
ccgtcctcct ttcctccctt tttccttccc atctctcagt tgtaccctttt ttctataagt  22980 agtcctttgg catttcgtat ataagaggtc acaaaggaat ttgagattgg gaagggattt   23040
ctttctgaaa cagagtctca ctcagtaccc aggctggagt gcatgggcat gactcactgc   23100
attttgaggt agctcactgc aacctcaaac ttctgggctc aaggaatcct cccacctcag   23160
cctcctgagt agctgggact gcaggcacac agcatcatgc cctgctaatt tttaaatttt   23220
ttgtagagat gagaacttgg tatgttactc aggctggtct tgaactcctt ggcacaagca   23280
atcctcccac ttcagcctcc caagtgccg agaccacaga tgtacaccac catgcctggc   23340
taattttcct tttctttttt ctttgtagag gcagggtctt gctattttt ccaggctggt   23400 cttgaacttt tggacttaag caaccctccc acctcggcct tctagagtgc tgggaagttg   23460
gggagggatt tctatacttg gcttctaagt tcccttagg ggatattttc accccacag    23520 ttaccttgag ttctgttgta ctattccagc cttcattgat gtttccttct ccgaattcat   23580
```

```
actgccttgg ttgttttttt gttttttgctt ttttgagaga gggtctcagt ctgttgccca   23640
tgctggagta cagtggcatg actatggctc actgaagtct caacctctca ggctcaagca   23700
gtcctcccac ctcagcctcc tgagtagcag gactacagat gcatgccacc agccttgact   23760
aattaaaaaa aaaaaaattt tttttttttt aattttttt tgtagagaca gggtcttccc   23820
atgttgccta gactggtcgt gaactcctca atgcaagtga tcctcccgcc tcagcctccc   23880
aaagtgctgg gattgtagac ataagctgcc gcacctggcc tgccttgatt tttaatttag   23940
tatttgctgc tttgtgttat ttatcctctc tcgttttga agacaggtac catgtctcat   24000
atctattctt ggtgcctgcc ttagctccat gttagggta gttactcaaa ggtgtattaa   24060
tcatattgtc tgtcaaaagc tgttacttat cttttgggct ctgtataatt ttatacttac   24120
atgtagtatt tgttcttatt taactcctga tttgttagat gtctcaagtg attcatgtta   24180
tactcaagtg tcaagtggct tttttggaa actatgctga aggtctaaat atttcttaag   24240
cttggccggg cacggtggct cacgcctgta atcccagcac tttgggaggc cgaggtgggc   24300
agatcacgat gaggtcagga gatggagtcc atcctggcta acacggtaaa accccgtctc   24360
tactaaaaat acaaaaaatt cgccaggcgt ggtggtgggt gcctgtagtc ccagctactc   24420
gggaggctga ggcaggagaa tggcatgaac ccgggaggtg gagcttgcag tgagcggaga   24480
tcacgccact gcactccagc ctgggcgaca atgagactcc gtctcaaaaa aaaaaaaaa   24540 tttcttaagc ttaatgttta caatgaagtc atatcaaaga aacacgttaa aacattctta   24600
aacactgagg ggccagtgtg taaggaagtc ttgctgtcca tattcactga gacatttcat   24660
ttaatatctt ccaaacattc agtaggtatc tgggtctcta cttatgtccc attctctgtg   24720
agagatgcag agatgaatca gatatgaatc ctggtcccag ggccctata atctagtagg   24780 taaataagat gcctttacca tcaaagccta caatttcagt acaatccttt ttacaattca   24840
cataaggtca aagtgatttg ggatttgagg aagaacaat tactaaatac agaccatgta   24900
tgaaactctg taggacaccc atctggtgtc cctgatagga ggaaaacttt gcatatgcac   24960
ataaaaattt aattttcctt cttcagtttt ttatacacag tatctggccc atagaattct   25020
gtatttgttg agtgaataca tgatacagta ttgccagtag tatattgcat accaaatgag   25080
gtatatggac aaaattaaag gagaggagat gactgtggac tgctgtagtc tcaagtgagt   25140
tcatgcagct tggaggggt gggatataac taggccctaa gaaatggatg ggaattcgtc   25200
agtaacaggg atgggaactc ttctgtaatg ggtggcaggg agttgggga gcagggtca   25260 ttggaaagca tagcttgagc aaagtctaga gtcaaggaaa tgcatatgtt cttcaggcag   25320
aaagatttca ggaaatggag caatgagtga taatgtaaat attgcactgc tggattcatg   25380
agagttataa ataccaccgg gcgcggtggc tcacgcctgt aattccagca ctttgggagg   25440
ccaaggcggg tagatcacct gaggtcagga gtttgagacc agcctggccg acatggtgta   25500
ccccgtgtct actaaaaata caaaaattag ctgggtgtgg tggcgcctgc ctgtaatccc   25560
tgctactcag gaggctgagg caggagaatt gcttgaacct gggaggcaga ggttgcagtg   25620
agccgaggct gtgccattgc actccagcct aggcaacaag aacaaaactc catctcaaaa   25680
aaaaaaagaa cttggacttt atgttgtggc taatgggagc caactgaaag tttttcatca   25740
acagagtaac atgaaccagg tgcagtctct cacacctgta atcccagcac tttgggaggc   25800
tgaggtggga ggattgcttg agcccaggag ttcaagacca gcctgggcaa tatagtgaaa   25860
ccctgtctct acaaaaaatt aaaaaattat tcaggcatgg tggcatgcag ctgtagtccc   25920
```

```
aactacttgg ggcagtgagg tgggaggatc gcttgagcct cagaggtcaa ggctacggtg   25980
agtcatgatc acgccaccac actccagctt gggcaatgga gcgagaccct aagctccaaa   26040
aacaaaaaaa tagagtatca tgacaaagca gttatcaatg tcacaaatcc tcaataaagc   26100
tggggagcag gtcaggtgca gtggctcgtg cctgtaatcc cagcactttg ggaggccgag   26160
gcaggtggat cacctacggt caggagttca agaccagcct ggccaacctg gtgaaaccct   26220
gcctctacta aaaatacaga aattagccag catggtggt gggtgcctgt aatcccagct   26280
acttggaagg ctgaggtgga agaattgctg aacctggga ggtgcagatt gcagtgagcc   26340
aagatggcac cactgcactc agcctgggtg acagagcgag actccatctc aaaaaaaaaa   26400
aaaaaaaagg ccaggcgcgg tggctcacgc ctgtaatccc agcactttgg gaggccgagg   26460
cgggcggatc acgaggtcag gagatcaaga ccatcccggc taaaacggtg aaaccccgtc   26520
tctactaaaa atacaaaaaa ttagccgggc gtagtggcgg gcgcctgtag tcccagctac   26580
tcgggaggct gaggcaggag aatggcgtga acccgggagg cggagcttgc agtgagccga   26640
gatcccgcca ctgcactcca gcctgggcca cagagcgaga ctccgtctca aaaaaaaaaa   26700 aaaaaaaaa aagctgggaa gtgattccaa caaactttat cttttttctt ctttatattc   26760
acccctctct tcctacccca cttcaatcct tccttctatc cattattttg gtctagttgt   26820
agtataaata catgtaatag agatataatt gtaactctct tttaggtgta gtctcttgcc   26880
ctacaaaatt tggtttcctg gccgttgtct tccatggaaa atttagacat aacaagaagt   26940
gtcacaaaat catgatactg ctataccatg tgcctgattt caataccagg ttgaatgaga   27000
tgatggaacc ttcctcatgg aatttggaga gatttatccc tagggcatt gtagatttaa   27060 tctaaggctg aactatcaaa tgaaactatt ggcaaaatta acccacagtt ctacttttac   27120
ctaaatctat gactaaagaa aactaaggag ctcttagttt tttccctggt cacctcctaa   27180
gacatgctat gatgaataag aaaatatttt ctgaatactg gtttgttgga agaatgtgat   27240
cagcttattt attttttgtta tctaaggaat ttaaaaactg gtcaactcct gaaaagatg    27300 cacattgatg attcttacca agcttcagtc tgtcacaaag cctattctga aatggtaagt   27360
aatgactggc tgggaccact ttgtgtgtta ctgttggtct cattaagtga gagcagtaag   27420
tcataagcag taatgaacaa accttccccg tggcatcttt tttcaaaatt ggatagcaat   27480
gtttgtcctt tcttgaaatt taggatgaaa ataagtgttg gtacagtgat tgcttggtaa   27540
attttctggc tgtaggacct gagggcaaat atttatttct agctgtggat ttgaactgag   27600
aactattatg cctgttatca gacttgactc ccagccacat tgccatgttt aagtagcctt   27660
aggaaggatg attaaatgat ccaataatcc cagaaatact tttttttttt tttgggatgg   27720
agttttgctc ttgttgccca ggctggagtg caatggcgcg atctcagctc actgcaacct   27780
ctgccttcta ggttcaatta attgtcctgc ctcagtcttc caagtagctg ggattacagg   27840
tgcccgccac cacacccggc taattttttgt atttttagta gagatggggt tttgccatgt   27900
tggccaggct tgtctcgaac tcctgacctc aggtgatcca cccgcctcag cctcccaaag   27960
tgctggtatt acagatgtga gccacagtgc ccagctaaca tgctttactc ttaggcttca   28020
gtcttctcac acagaaataa atacagttac tcagctcttg cactaatagt cttggctagt   28080
gggtacaaac atacagttag aaataagctc caatattcag tagcagagta gaatgactgt   28140
agttagcaac aatgtgctat atatttcaaa gtagctagaa gaaaggactt gaaatgttcc   28200
caatacatag aaatgataga ttctcgaggt gatgggtacc ccaaataccc cgccttgatc   28260
attatatact ttgtgcacat aacaaataca tgtaccccat aaatatataa atatttttgt   28320
```

-continued

```
attaataaaa aaaaaaaaac gctttgggag gccaaagtgg gtggaacacc tgaggtaagg    28380
agtttgagac cagcctgacc aatatggtga agcccacct ctactaaaaa tacaaaaatt    28440
aggtgggcgt ggtggcgcat gcctgtaatc ccagctactt gggagactga ggaaagagaa    28500
ttgcttgaac ccaggaggcg gaggttgcag tgagccgaga ttgcacgatt gcactccagc    28560
ctgggcgaca gagcgagact ccgtctcaaa aacaaaaag aaaaaaaaaa agtttttacct    28620 tgggcaatgt ggcaaaaccc catcactata aaaaagaca aaaattagcc aggcatggtg    28680
gcatgcagct gtagtcccag ctactcagga ggctgagttc aggggatccc tggagcccag    28740
gaggtcgagg ctgtggtaag ccatgatcac actgctgtac tccagcctgg gcaacagagt    28800
gggaacctgt ctcaaaaaaa aaaaaaaaa aaagtcttg gcctggcatg gtggctcaca    28860
cctataatcc cagcactttg ggaggccgat gtgggtgtat catgtgaggt cagtagttcg    28920
agaccagcct ggccaacatg gtaaaacccc gtctctacta aaactacaaa aattagccag    28980
atgtcatgtc aggcacctgt aatcccagct actcaggagg ctgaggcagg aagaattgct    29040
tgaacccagg aggtggaggt tgcagtgagc cgagatcgtg ccactgcacc ctgggtgaca    29100
gagcaagact ctgtctcaaa ataaataaat aaataaataa aaagccttga ctcacaatct    29160
agttacagtg ggaaagtagt tgtctaggag taatgaataa ctacttgagt attcactgtt    29220
gaagccatga gcagagacaa tggcagcagg ctcagcattt gtgtagagac tgacttgcct    29280
ggtgattaca gtgagaggat cagcatccag aggctctgaa cacaaagacc gcatctttcc    29340
ctagcctagt aggatctgtg gaattgaatt taaaagttgt gtgatgttat ataatccaac    29400
acataatctt gagcctaacc tttgtcctcc tttaaataag acagttgtgg ccaggtgtag    29460
tggcacatgc ctgtaatacc agcttctcca gtgagaggat cactggagcc caggtgttcc    29520
aggctgcagt gagccatgat ggcaccactg tactccagcc tgggcgatag agtgagaccc    29580
tgtcccaaaa ataactaata gtccaggtgc agtggctcac gcctgtaatc tcaacacttt    29640
gagaggccaa ggcgggtgga tcacctgagg tcgggaattc aagaccagcc tggccaacat    29700
ggtgaaaccc tgtctctact aaaaatacaa aatttacatg ggtgtggtgt gtgcgcctgt    29760
agtcccaact actagggaag ctaaggcagg agaattgctt gaacccaggg ggcagaggtt    29820
gtagtgagcc gagagtgtgc cactgcactc cagcctgagt gacaagagca aaactccatc    29880
tcaaaaaaaa ataataataa taataataac taggctgggc atggtggctc acgcctgtaa    29940
tcccagcact ttgggaggct gaggcaggtg gatcacctga ggtcaggagt tcaagaccca    30000
gcctgaccaa catgatgaaa ccctgtctct actaaaaaat acaaaaatta gctgggcatg    30060
gtggcaggtg cttataatcc cagctactca ggaggccgag gcaggagaat cacttcaacc    30120
tggaggtgga ggttgcagtg agccaagatc gtgccattgc actctagcct gggcgacaga    30180
ggaagactct gtctcaaaac aaaagaacaa caacaacaac gaatagatag attgatagat    30240
agatagatag atagatagat agatagatag atagatagac tgacagttga attcatctct    30300
agaatttact ttttttttga gacaagattc ttgctctgtc acccaggctg gagtacagtg    30360
gtgtgatgtc ggctcactgc aacctccgcc tgccaggttc aagcaattct gtgcctcagc    30420
ctcccaagta gctgggatta caggtgtgcc tgccgccatg cctggctaat ttttttgtat    30480
ctttagtaga cgggggttt caccaagttg gccaggctgg tcttgagctc ctgactttgt    30540
gatccacccg cctcacgctc ccaaaatgct gggattacag gcgtaagcca ccatgcctgg    30600
cctagaattt acttattaag catttaaata atgttatacc ttttatatta caacatcaat    30660
```

```
acccacttga tattaaaaca tttcacacag acatgtgtaa gatagtaagt aaaagtcccc   30720
cataaagcca atcttcagaa ataatattta atgccaggcg tggtggctca cacctgtaat   30780
cccagcactt tgtgaggccg aggcgggcag atcacgaggt caggagattg agaccatcct   30840
ggccaacatg gtgaaactcc gtctctccta aaaatacaaa aattagctgg gcatggtggt   30900
gcgcacctgt agtcccagtt agttgggagg ctgaggaagg agaattgctt gaatccagga   30960
ggcagaggtt gcagtgagac gacatcctgc cactgcactc cagcctggcg aaaaagcaag   31020
tctctgtctc aaaaaaaaa aaaaaaaga aataacattg tattatttat ttaactgttt   31080
agtgcaggga ttgataaact ttttccatat atgaccagac ggcaaatact ttcagctgtg   31140
ctggccttac aatctctgtt ttacatactc aactctgcca ttgtggcccc aaatcagcca   31200
tagactgtat gcaaatggat agatgtagct gtgttctaat aaaactttat ggagactgaa   31260
acttgaactt catatgttaa ttttggcatg tcacaaaatg ttattttttct gatgttttttc   31320 agccatttca aaatctgaaa acattcttta gtttattagc catggaaaaa taagcactgg   31380
ggccaggcat ggtggctcac agctgtaatt ccagtgcttt gggaggccaa ggagggagga   31440
ttgcttgagg ccaggaattc aaggctgcag tgagctgatt atgccactgc actccagcct   31500
aggtgacagt gagaccctat cccccaaaaa aaagtgttgg gtggccaggc gcggtggctc   31560
acgcctgtaa tcccagcact ttgggaggct aaggcgggcg gatcatgagg tcaggagatc   31620
gagaccatcc tggctaacac agtgaaaccc cgctctacta aaagtacaaa aaattagccg   31680
ggcgtggtgg cgggcgcctg tagttccagc tactcgggag gctgaggcag gagaatggcg   31740
tgaacccagg aggcagagct tgcagtgagc agacatcgca ccactgcacg ccagcctggg   31800
cgacagtgca agactctgtc tcaaaaaaaa aaattgtgtt gggttagatt tacctggtgg   31860
gccatagttt gtcagcctct tcttaactgt atagcattta acattttttaa atcctcagtt   31920 ttttcccttt ttagagatag ggtctcactc tctcattcag gctgtagatc agtggcacca   31980
tcatagctca ctatagcctt gagttcttgg gctcaagcga tcctcccac tcagcctgcc   32040 aagttgatgg gattacatgg catgagccac agcacccagc taaatttaa tttaattttt   32100 ttagatgatg aggtcttcag ctgtgttttcc caggcttgtc tcaagctatc ctactgcctc   32160
ggcctcctga gttacctcag ttgttttcta aatataaaaa tattttattt tcattaataa   32220
attcaatcat ttgacctgac gccgtggctc acgcctataa tcccggccct ttgggaggct   32280
gaggtgggtg gatcacaagg tcaggagatc gagaccatcc tggtcaacgt ggtgaaaccc   32340
tgtctctact aaaaatacaa aaattagcca ggcatggtgg cgcatacctg taatcccagc   32400
tacttgggag gctgaggcag gagaatcact tgaacctggg aggcggaggt tgcagtgagc   32460
tgagatcgca ccattgcact ccagcctggg caacgagcga aactccgtct caaaaaaaaa   32520
aaatctgtat atatgtgtgt gtgtgtgtgt gtgtgtatat atatacacac atacagtaat   32580
attattatta gagcctgtaa ttttaaagcc aggagagaac tttaacacat tttctcacag   32640
aaacagccat aggtgatggt atcttttttt ggtcacccttt attcatagag agtagtaggg   32700
tcagggtttt aaataggcta ttgtgggctg gtctgagaaa ccagccacca tgtacaagat   32760 tgttttatg ggaaaacatg ttctgaatgt tcaaaaacca atttacaaat gaatatttct   32820
aatttgagca ctccctgcac atgtgtgtcc tcattctctc tttgccaata tttcccaaaa   32880
tgaatggcat gaaatgtagt actatctaag gggaaggaaa tggatgaatc agattcatgc   32940
ctggcaagac tggctaaaac aaacactggg aaccggaagc aggagaagct aaagctagaa   33000
gttggctgag cgcggtggct gacgtctgta atcccaacac tttgggaggc tgaggtggga   33060
```

```
ggatcccttg aggccaggtg ttcaacaaca gcctgggtaa cacaggaagg ccttgtctct    33120
aaaaaaaaaa agaagaagaa caagaagcca gaagtccagt ccagtaataa tctcaacagt    33180
tcctagacgg cagggaaaaa aatcaagcca gtggttaaat cctggatact tcagagccta    33240
tcggtcattg ctttaattgt ttggtttttg tctctgccag atctttattt ttcctgacat    33300
actcttgaca gtctatttgg gatatttatt tttctccgaa attaggggct tctctttatt    33360
gtcctgagtc atccctgtgc caaagagagt gagtcgttgc gaagccctgt gtttcagctc    33420
attgtgatta accctaagac gactctcagc gtgggtgtga tgctgtactg tcttcctcca    33480
gggcaggctg gcaggcaagt gtgcataact gctactctat gggtgggaca ttctgaaagg    33540
cactgtgcaa acacaaaaac tagatatttt tgtgtcactt agaagaatgg aaaacatgaa    33600
atactatata tcatgatagg aatattcaga agtaggatga agattagtgg acttgagtca    33660
aaccccagat tccctgcatc ctgatctcta ctagtatggg gttatatagg ttttttaatag   33720 tgtttattca agccctgttt tttcccctaa ggtaaatatt ttggcagcac atggtggatc    33780
atgcctgtaa tcccagcact tgggaggtc  aaggtgggag gagagcttga gcccaggagt    33840
ttgagaccaa cttggacaac agagcaagac ccagtctcta ccaaaaaaaa tatatatata    33900
tattagccaa acatgctggc atgcatctgt acttccagct actcgggagg ctgaggtggg    33960
aggatggctt gaacctggga ggtggaggct gcagtgagcc gaaatcatac cacttcactc    34020
aagcctggca acagagcaag accctgtctc aaaaaaaaaa aaaaaaaat  tcacataaag    34080 agtaatgaac gttctgtatt taaaaaacat aatttgtgtt ctttccctaa acctaaatta    34140
aggaaaattt aaggtacttt aggaagacat ctttactttg aaatctgact gagtttgact    34200
gagcctctat catgcaggca gtttatattt atctatagat aagtatttat ctggccaggc    34260
agtggctcac gcctataatc ccagcaattg ggaggctgag gcaggtgcat catgaggtca    34320
ggagttcacc agcctggcca agatggtgaa accccatctc tactaaaaat acaaaaatta    34380
gctgggcacg gtggcaggca cctataatcc cagctactcg ggaggctggg gtcacttgaa    34440
cctgggaggc agaggttgca gtgagccgag atcgtgccac tgcactctag cctgggagac    34500
agagcgagac tccgtctcaa aaaaaaaaa  aaaaaagcag ggtgcagtgg ctcacgcctg    34560
taatcccagc actttgggag gccgaggcag gcggatcatg aggtcaggag ttcgagacca    34620
gcctgaccaa cacggtgaaa ccccgtctct actaacatac aaaaattagc tgggcatggt    34680
agtgcgtgcc tgtaatccca gctactcagg aggctgaggc aggataatcg cttgaacccg    34740
ggagggagag gttgcagtga gccgagattg taccactgca ctgcagcctg gctgaagtg     34800 aatcaagaaa acaaggtctg actttaataa ctcacaagga taatgcacac agttacaata    34860
catgtttttt tggaccttat gcaaagttta tttgataagt gcatgttcta aaagacattc    34920
tctatcccta tgcacttagc tagctgtgac acttctgcag ggtcttgctt tgttgcccag    34980
gctggagtgc agtggcacga tctcagctca ctgcaactct gcctcccggg ttcacaccat    35040
cttcccatct cagcttccca gtagctggg  actacaggta catgccacca cgcttggcta    35100 atttttttt  tttttaagaa cctaagaacc tcagaactat catctgcagt atgtgctttc    35160
atataaaact tgcttccttg gatttgaaga gagaacgata gtcgttggcc ctagagatta    35220
aagataaaga taactgcttg gtcaagcatt tcctttgtca cttttcaaac tcatctgttc    35280
aggaatcctt gaaagcctgt ttggtaccaa tcctgtagga agcatatctt agttctatta    35340
ggctgctaca acaaaatacc acagactggg tagcctttaa acaacaaagt gtatttctta    35400
```

```
ccattctttt ggctgggaag tccaagatca aggtgctggc ggattcactg tctggtgaga    35460
gcccatttcc tggctcatag atgtgtcctc acatggtaga aggcagcttt ctggggcctg    35520
ttttacaaaa ccaccaatca cttctcaaaa gccccacctc ctaataccat cacattggtg    35580
attaggtttc aacagattaa tcttgggagg acacaagcat tcagaccata gcaaaacact    35640
gctatttctg gccgggcgcg gtggctcatg cctgtaatcc cagcactttg ggaagccgag    35700
gcgggcagat cacttgaggt caggagttcg cgaccagcct ggccaacatg gtgaaaccct    35760
gtctccacta aaatacaaa aatgagctgg gtgcgatggt gtgcaccagt aatcccagct    35820 attgggagg ctgagacagg agagtcactt gaaactggga ggcagaggtt gcagtgagct    35880
gagatctcgc cattgcactt cagcctgggt gacagagcaa ggctctgtct caaaaacaaa    35940
caaacaaaca aaccacttat ttctaatttt atggaaatta gaagggaaaa ctagtgactg    36000
ttgttcagtg cacaaaatac aatacatgaa gcttgcactg tttgagagca caagagtgga    36060
gaggtgggca ccttaattgg cagtagaggg ttggggagag actgtcaaag aaaaccttag    36120
ggagtttcca aagataagtt aggagttagg tacgcaaagt tgggtgggaa ccagggataa    36180
aaagtatcat gcagttcatt catataaatac tctttggaga gctggccatg cctcaggcac    36240
cagtgataca gcagtgaata ataataatag ctaattttt ttttgagacg gagtttctct    36300
ctgttgccca ggctggagtg cagtggcatg atctcagctc actgcaacct ctgcctccca    36360
ggttcaagcg atcctcttgc ctcagccccc ctagtagctg gattacagg cacgtgccac    36420 catgcccagc taattttgt attttagta gagacggggt ttcaccatgt tggccaggct    36480
agtcgtgaac tccttacctc agtgatctg cctgccttgg cctcccaaag ttctgggatt    36540
accggcgtga gccaccagc ctggccacaa taacagctaa ttttttttt tggagacagg    36600 gtctcacttt atcgcccagg ttggagtgca gtggcacgat cttggctcac tgcaacctcc    36660
acctcccatg ttcaagcaat tcttgtgctt cagcctcccg agtagctggg attacaggca    36720
tgtgccacca cgcctggcta attttgtatt tttagtagag accgggtttc tccatgttgg    36780
ccaggctggt ctcaaactcc caacctcagg tgatccaccc gccttggcct cccaaagtgc    36840
tgggattaca ggcgtgagcc accacacccg gctaataata gctaatttt attgagcacc    36900 tcctgtgtgc caggcactgc gctaagcctt ttataggaac tgtttcattt aacctcacca    36960
cagtcctgtc aagtatgtgc tcttaaaatc atccctattg tactgataaa gttaaataat    37020
ttgcccaggg ttgcacagct cttactttgt agagttagaa tttaaaccca ggtagctgac    37080
tgcagagccc ttgtctaaat gaaaaaggca accaggtagg tttctgcttc atagatggca    37140
tcttttgtgg gggaaattcc cactgaatat ggaaacaggg taatctcaaa tagtgaaaag    37200
tgcaatgaag ataaaaacat atatgtcata aagatggaac agatcccgta tgtgtgtgca    37260
cactgcctga gatagaggat taggggtgac ctttctatgg acataacagg cctgaatgat    37320
gacaagaact cagccatgct aagagctggg gtgagagcct gtcagggaga aagaatggca    37380
agagcagtga cactgagttg ggactgagtt tggccagagt gatggagagt ggaaggaagg    37440
ccactgtgcg ccagccttca attgctacaa gatgcatcag agagattggc aggaactgga    37500
catgtgattc tgtccaaaac tgcaacacaa tagccaacag acctctaagg ctacaaatgt    37560
aggcattcat agttacaggg attttgttc ctgttgctgg ttttgggaac atggttttga    37620
cctttttttt tttttaatt gttttttgga tatgtaatct gaattatatc ttctttgtat    37680 gctatccaggt tcctgaagg tgacgtgaaa gatcactgtg cagcagcaat cttgacttct    37740
ggaacaattg ccatttggga cttacttctc ggtcagtgta ctgccctcct cccacctgtc    37800
```

```
tctgaccaac attggtcttt tgtgaaatgg tcgggtacag actctcattt gctggctgga    37860
caaaaagatg gaaatatatt tgtataccac tattcataag ttagggtaaa gtgaaaacac    37920
aattttctgg atatattggg cctcttagta tttttggag ttttaaatat aaaggagaat     37980
atctgaatga cacttaaaat gattgcttgt ttatgtccag acagacttat tttttattct    38040
aatgatggta gcaccactga tcttggatgt acatttatgt atactttgag aaaaagggtt    38100
ttaggttgat ttttgtaatt tcccacattt gtacatgtgc ttttaaaggt gtacataaag    38160
cttcaaatgg caataaatat ttatttttat acattc                              38196
```

DIAGNOSTIC METHOD USING PALB2

This application incorporates expressly by reference the content of U.S. patent applications Ser. No. 61/157,700 filed Mar. 5, 2009 and Ser. No. 61/264,019 filed Nov. 24, 2009.

STATEMENT GOVERNMENT INTEREST

Funding for the work described herein was provided, in part, by the federal government, which may have certain rights in the invention according to the terms of National Institute of Health grants CA62924, CA123483, and RO1CA97075.

FIELD OF THE INVENTION

The invention generally relates to personalized medicine, and particularly to method of diagnosis in pancreatic cancer.

BACKGROUND OF THE INVENTION

Pancreatic cancer is one of the most deadly cancers, in part because it is often undetected until an advanced stage. If a patient is diagnosed at a late stage, the survival rate at five years after diagnosis is only about 5 percent. Early diagnosis at an early stage however can lead to significantly improved survival outcome. It is estimated that as many as 10% of pancreatic cancers are familial or hereditary. For familial pancreatic cancer, if a predisposition in a patient having a family history can be detected before cancer develops, then early start of surveillance and screening could increase the chance of early diagnosis and improved prognosis. Five different genetic syndromes have been associated with predisposition to pancreatic cancer. These include BRCA2 mutations, familial atypical multiple mole melanoma (FAMMM), Peutz-Jeghers Syndrome, hereditary pancreatitis, and the hereditary non-polyposis colorectal cancer (HNPCC) syndrome. See e.g., Tascilar et al., *Anal. Cell Pathol.*, 19(3-4): 105-10 (1999). However, many familial pancreatic cancer cases can not be explained by any of these five genetic syndromes. Clearly there is a need to identify additional genetic predisposition markers for pancreatic cancer.

Another difficulty in pancreatic cancer is that there is no effective treatment for advanced pancreatic cancer. Gemcitabine, the current standard of care, results in an average progression free survival of 3-4 months and median survival of 5-6 months. See O'Reilly, *Gastrointest. Cancer Res.*, 3(2 Suppl):S11-5 (2009. Second line treatment after gemcitabine failure is even less effective with median survival of approximately 3 months. See, Moore et al., *J. Clin. Oncol.*, 25(15): 1960-6 (2007); Philip, *Gastrointest. Cancer Res.*, 2(4 Suppl): S16-9 (2008). One strategy actively sought to improve outcome is to personalize patient treatment. In recent years, with the ability to interrogate the entire human cancer genome, it is becoming apparent that some cancers can be effectively treated by targeting specific somatic genetic alterations present in the cancers. This is perhaps best exemplified by the observation that patients with lung cancer harboring mutations in the epidermal growth factor (EGFR) gene respond rather dramatically to agents that target this receptor. Lynch et al., *N. Engl. J. Med.*, 350(21):2129-39 (2004); Paez et al., *Science*, 304(5676):1497-500 (2004). Clearly, there is also a need for biomarkers predictive of therapy outcome and useful in personalized pancreatic cancer treatment.

BRIEF SUMMARY OF THE INVENTION

The inventors have now surprisingly discovered that PALB2 mutations are associated with a predisposition to pancreatic cancer. PALB2 appears to be the second most commonly mutated gene for hereditary pancreatic cancer, after BRCA2. The inventors have also surprisingly discovered that some pancreatic cancer patients harbor somatic PALB2 mutations in their pancreatic tumors. In addition, it has also been surprisingly discovered that pancreatic cancer patients having PALB2 mutations are especially responsive to treatment with a DNA damaging agent such as mitomycin C and cisplatin.

Accordingly, in a first aspect of the present invention, a method of detecting mutation is provided comprising identifying a patient diagnosed of pancreatic cancer, or having an increased risk, or a family history of, pancreatic cancer, and determining in a sample obtained from the identified patient the presence or absence of a mutation in the PALB2 gene or a reduced level of PALB2 gene expression. Optionally, the method includes a step of identifying or diagnosing a patient as having pancreatic cancer or having a family history of pancreatic cancer.

In another aspect, the present invention also provides a method for diagnosing a predisposition to, or increased risk of developing, pancreatic cancer in a patient, comprising detecting in a non-tumor sample or tumor sample obtained from an individual, a mutation in the PALB2 gene or a reduced level of PALB2 gene expression, wherein the presence of the mutation or reduced level of gene expression would indicate a predisposition to pancreatic cancer. The method for diagnosing a predisposition to pancreatic cancer according to the present invention may optionally further include a step of placing the diagnosed/identified individual under a "preventive regimen" such as increased surveillance for pancreatic cancer using diagnostic markers such as CA19-9, or frequent image scan (e.g., CT and ultrasound), or administration of preventive pharmaceuticals or nutraceuticals (e.g., vitamin D, and B vitamins such as B12, B6, and folate).

In yet another aspect of the present invention, a method is provided for predicting an individual's response to therapy. The method comprises detecting in a sample obtained from a pancreatic cancer patient, a mutation in the PALB2 gene or a reduced level of PALB2 gene expression, wherein the presence of the mutation or reduced level of gene expression would indicate that the individual has an increased likelihood of responding to a therapy that induces DNA damage or interferes with DNA damage repairs in tumor cells. Again, the sample used can be a non-tumor sample or a tumor sample.

The present invention further provides a method of treating pancreatic cancer in a patient, comprising administering to a patient identified as having a germline or somatic mutation in a PALB2 gene or a reduced level of PALB2 gene expression, a therapy that induces DNA damage or interferes with DNA damage repairs in tumor cells.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 2 are images of clinical outcome in the patient who was found to harbor a PALB2 mutation and was responsive to mitomycin C (MMC) and cisplatin.

FIG. 4A is a schematic diagram showing the somatic mutation found in the PALB2 gene of the patient treated;

FIG. 4B is gel image of showing the co-immunoprecipitation with a monoclonal antibody against BRCA1 of the BRCA1-BRCA2 complex. No complex is identified in the PALB2 mutant tumor JH033 as compared to the wild type Panc185 tumor used as a control; and FIG. 4C is a Western Blot image for FANCD2 ubiquitination. The upper band represents the ubiquitinaed or long form (P-FANCD2 Lys561) and the lower band represents the short, non ubiquitinated form. JH033 has competent proximal FA complex similar to the MMC resistant Panc185 control.

DETAILED DESCRIPTION OF THE INVENTION

Figure 1:
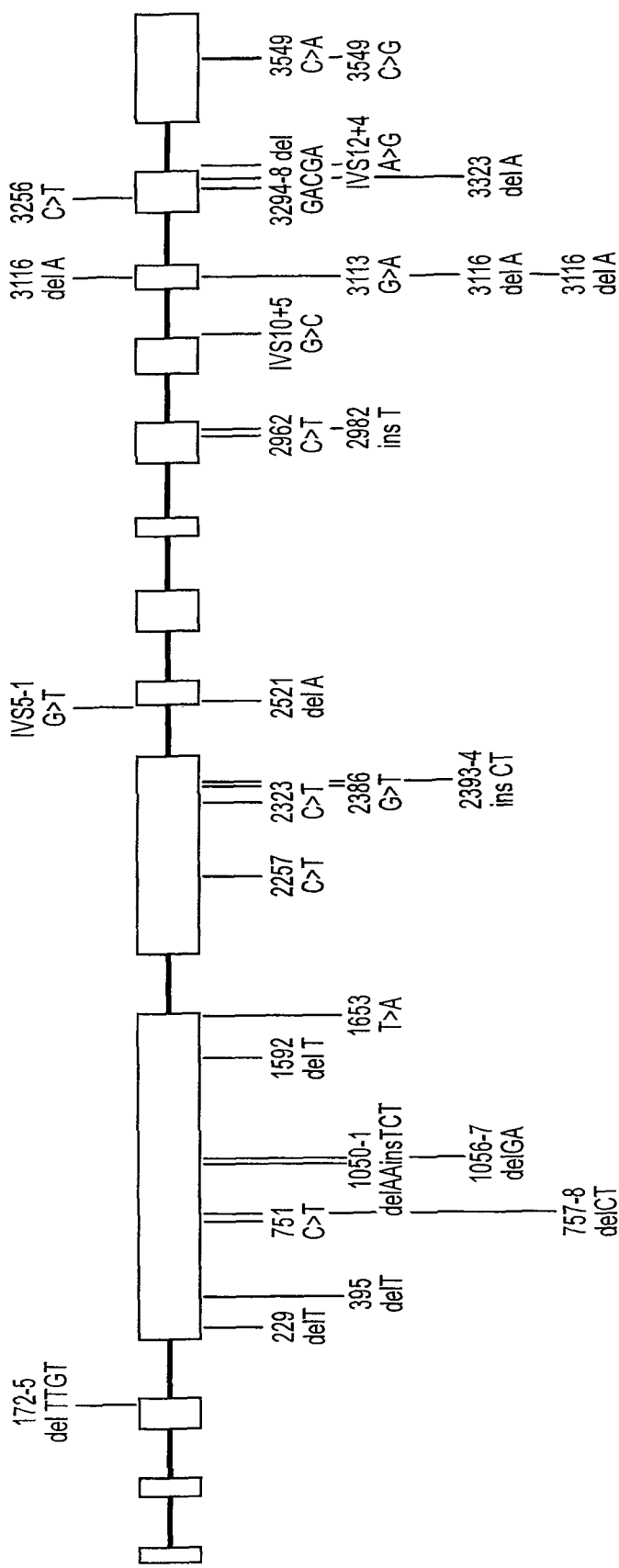
FIG. 1 is a schematic diagram showing the location of identified PALB2 mutations. Exons are represented as boxes and introns as black lines (not to scale). Mutations previously identified in patients with familial breast cancer or Fanconi Anemia are shown in black or purple, respectively. Germline mutations identified in patients with familial pancreatic cancer are shown above the gene in red.

In accordance with a first aspect of the present invention, a method of detecting mutation is provided comprising identifying a patient diagnosed of pancreatic cancer, or having an increased risk of developing, or having a family history of, pancreatic cancer, and determining in a sample obtained from the identified patient the presence or absence of a mutation in the PALB2 gene or a reduced level of PALB2 gene expression. Optionally, the method includes a step of identifying or diagnosing a patient as having pancreatic cancer or having a family history of pancreatic cancer.

The present invention also provide a method for diagnosing a predisposition to, or an increased risk of developing, pancreatic cancer in a patient, comprising detecting in a non-tumor sample or tumor sample obtained from an individual, a mutation in the PALB2 gene or a reduced level of PALB2 gene expression, wherein the presence of the mutation or reduced level of gene expression would indicate a predisposition to pancreatic cancer. In various embodiments, the individual tested can be healthy and free of family history, or diagnosed of pancreatic cancer, or is suspected of having pancreatic cancer, or has a family history of pancreatic cancer. Preferably, a non-tumor sample, i.e., normal tissue or bodily fluid sample is used in the method. In non-tumor samples, a mutation detected would be a germline mutation.

Once an individual is identified as having a PALB2 mutation or a reduced level of PALB2 gene expression, and thus having a predisposition to, or an increased likelihood of having, pancreatic cancer, the individual can be placed under a "preventive regimen." Thus, the method for diagnosing a predisposition to pancreatic cancer according to the present invention may optionally further include a step of placing the diagnosed/identified individual under a "preventive regimen." As used herein, the term "preventive regimen" means any preventive measures suitable for early detection of pancreatic cancer, or preventing or delaying the onset of PALB2-associated pancreatic cancer. For example, increased surveillance for pancreatic cancer using diagnostic markers such as CA19-9, or image scan (e.g., CT and ultrasound) can be used for this purpose. Alternatively or concurrently, pharmaceuticals or nutraceuticals (e.g., vitamin D, and B vitamins such as B12, B6, and folate) can be administered to the individual to prevent or delay the onset of pancreatic cancer.

In yet another aspect of the present invention, a method is provided for predicting an individual's response to therapy. Generally, the method comprises detecting in a sample obtained from a pancreatic cancer patient, a mutation in the PALB2 gene or a reduced level of PALB2 gene expression, wherein the presence of the mutation or reduced level of gene expression would indicate that the individual has an increased likelihood of responding to a therapy that induces DNA damage or interferes with DNA damage repairs in tumor cells. Again, the sample used can be a non-tumor sample or a tumor sample.

Accordingly, the present invention also provides a method of treating pancreatic cancer in a patient, comprising administering to a patient identified as having a germline or somatic mutation in a PALB2 gene or a reduced level of PALB2 gene expression, a therapy that induces DNA damage or interferes with DNA damage repairs in tumor cells. More specifically, a method is provided which includes generally the steps of identifying a patient diagnosed of pancreatic cancer, determining in said patient the presence or absence a defect in a PALB2 gene or protein, and if the defect is detected, treating said patient with a therapeutic regimen that induces DNA damage or interferes with DNA damage repairs in tumor cells.

In the various methods of the present invention described above, PALB2 mutations refer to alterations to the PALB2 gene including deletions, insertions, duplications, substitutions, etc. As will be apparent to skilled artisans, mutations resulting in significant reduction or loss of PALB2 protein or PALB2 function are most relevant in the methods of the present invention, particularly the PALB2 function in homologous-recombination-based DNA double-strand break repair (DSBR). See e.g., Xia et al., *Mol. Cell*, 22:719-729 (2006). In this regard, large genomic rearrangements (typically resulting in deletion or duplication of one or more exons), stop codon mutations, and frameshift mutations are clearly deleterious, as they typically lead to truncation of PALB2 protein and loss of PALB2 function. Biochemical and cellular assays may also be used to determine whether a particular mutation is deleterious or not. Such assays are known in the art and would be apparent to skilled artisans. Examples of PALB2 mutations include those in FIG. 1. PALB2 mutations such as 172-5del TTGT, IVS5-1 G>T, 3116delA, 3256C>T, and IVS10+2C>T are newly discovered by the inventors. Thus, in some specific embodiments of the methods of the present invention described above, the presence or absence of one or more such mutations are determined. The locations and identities of such mutations should be apparent to skilled artisans especially in view of the diagram in FIG. 1 and the publicly known reference sequences under RefSeq Nos. NG_007406.1 (genomic) and NM_024675.3 (cDNA/mRNA) in NCBI Reference Sequence Database. In this regard, the present invention also provides isolated nucleic acids (e.g., DNA) comprising a portion of the PALB2 gene sequence spanning and containing one of the mutations 172-5delTTGT, IVS5-1 G>T, 3116delA, 3256C>T, and IVS10+2C>T. Preferably, the isolated nucleic acids have a consecutive 17, 18, 19, 20, 21, 25 or 30 to about 100, 200, 300, 400 or 500 nucleotides of the PALB2 genomic DNA or cDNA, spanning and containing one of the mutations 172-5delTTGT, IVS5-1 G>T, 3116delA, 3256C>T, and IVS10+2C>T. In one embodiment, the isolated nucleic acid has from 18, 19, 20 or 21 to about 100, 200, 300 400 or 500 nucleotides comprising at least 18, 19, 20 or 21 consecutive nucleotides of SEQ ID NO:1 spanning the nucleotides T and C at positions 24 and 25, respectively of SEQ ID NO:1. In another embodiment, the isolated nucleic acid has from 18, 19, 20 or 21 to about 100, 200, 300 400 or 500 nucleotides comprising at least 18, 19, 20 or 21 consecutive nucleotides of SEQ ID NO:2 spanning the nucleotides A and T at positions 24 and 25, respectively of SEQ ID NO:2. In another embodiment, the isolated nucleic acid has from 18, 19, 20 or 21 to about 100, 200, 300 400 or 500 nucleotides comprising at least 18, 19, 20 or 21 consecutive nucleotides of SEQ ID NO:3 spanning the nucleotide T at position 25 of SEQ ID NO:3. In yet another embodiment, the isolated nucleic acid has from 18, 19, 20 or 21 to about 100, 200, 300 400 or 500 nucleotides comprising at least 18, 19, 20 or 21 consecutive nucleotides of SEQ ID NO:4 spanning the nucleotide T at position 25 of SEQ ID NO:4. In yet another embodiment, the isolated nucleic acid has from 18, 19, 20 or 21 to about 100, 200, 300 400 or 500 nucleotides comprising at least 18, 19, 20 or 21 consecutive nucleotides of SEQ ID NO:5 spanning the nucleotide T at position 25 of SEQ ID NO:5.

For purposes of the various methods of the present invention, the diagnosis of pancreatic cancer can be done by conventional diagnostic methods known in the art. For example, CA19-9 (carbohydrate antigen 19.9) is a tumor marker often used for the diagnosis of pancreatic cancer. Imaging studies, such as computed tomography (CT scan) is useful in the identification of the location of the cancer. Endoscopic ultrasound (EUS) can also help in visualizing the location and can guide a percutaneous needle biopsy. Biopsy samples can be used in pathological analysis for definitive diagnosis.

The identification of individuals with an increased risk of family history of pancreatic cancer should also be apparent to a skilled artisan. Typically, inquiries are made about an individual's family history of pancreatic cancer. If two or more first-degree relatives (sibling-sibling or parent-child) or second-degree relatives (uncle/aunt-cousin, grandparent-grandchild, etc.) in a family have been diagnosed with pancreatic cancer, then individuals in the family can be identified as having a family history of pancreatic cancer and/or as having an increased risk of pancreatic cancer.

In the various methods of the present invention, both mutations in the PALB2 gene and PALB2 gene expression can be analyzed in a patient sample by any suitable techniques known in the art.

"Sample" as used herein refers to any biological specimen, including any tissue or bodily fluid, that can be obtained from, or derived from a specimen obtained from, a human subject. Such samples include, healthy or tumor tissue, bodily fluids (e.g., blood), waste matter (e.g., urine, stool, sputum), buccal swap, etc.

For purposes of detecting mutations in the PALB2 gene, both genomic DNA and mRNA/cDNA can be used, and both are herein referred to generically as "gene." Numerous techniques for detecting mutations are known in the art and can all be used for the method of this invention. The techniques can be protein-based or DNA-based. In either case, the techniques used must be sufficiently sensitive so as to accurately detect the small nucleotide or amino acid variations. Very often, a probe is utilized which is labeled with a detectable marker. Unless otherwise specified in a particular technique described below, any suitable detectable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., *Nucleic Acids Res.*, 14:6115-6128 (1986); Nguyen et al., *Biotechniques,* 13:116-123 (1992); Rigby et al., *J. Mol. Biol.,* 113:237-251 (1977). The PALB2 gene is known in the art, and its genomic DNA sequence can be found under NCBI Reference Sequence (RefSeq) No. NG_007406.1. The Reference Sequence for PALB2 mRNA and protein sequences can be found under NCBI Reference Sequence (RefSeq) No. NM_024675.3 and NP_078951.2, respectively. Given such sequence information, methods of analyzing PALB2 genomic DNA, mRNA and protein should be apparent to skilled persons in the art. Particularly, skilled artisans would immediately be able to provide probes and primers for detecting PALB2 mutations and epitopes for developing antibodies for detecting PALB2 protein. The reference PALB2 cDNA sequence is provided in SEQ ID NO:6, and the coding sequence thereof is provided in SEQ ID NO:7. The genomic DNA sequence of the PALB2 gene is provided in SEQ ID NO:8.

In a DNA-based detection method, target DNA sample, i.e., a sample containing a genomic region of interest, or the corresponding cDNA or mRNA must be obtained from the individual to be tested. Any tissue or cell sample containing the relevant genomic DNA, mRNA, or cDNA or a portion thereof can be used. For this purpose, a tissue sample containing cell nucleus and thus genomic DNA can be obtained from the individual. Blood samples can also be useful except that only white blood cells and other lymphocytes have cell nucleus, while red blood cells are anucleate and contain only mRNA. Nevertheless, mRNA is also useful as it can be analyzed for the presence of mutations in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

Thus, preferably, all or parts of the PALB2 gene (genomic or cDNA) is amplified by any known nucleic acid amplification technique such as PCR, to a sufficient quantity and purity, and further analyzed to detect mutations. Preferably, genomic DNA is isolated from a sample, and all exonic sequences and the intron/exon junction regions including the regions required for exon/intron splicing are amplied into one or more amplicons, and further analyzed for the presence or absence of mutations.

To determine the presence or absence of mutations, one technique is simply sequencing the target genomic DNA or cDNA. Various sequencing techniques are generally known and widely used in the art including the Sanger method and Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and thus can also be used in the present invention. See Nordstrom et al., *Biotechnol. Appl. Biochem.*, 31(2):107-112 (2000); Ahmadian et al., *Anal. Biochem.*, 280:103-110 (2000). The obtained sequence is then compared to the wild-type or consensus sequences such as the relevant reference sequences found in Genome Browser database.

Mutation scanning in a target gene can also be economically accomplished by the dHPLC method. Specifically, the target gene is first amplified by PCR into different amplicons, and each amplicon is analyzed by dHPLC to detect the presence or absence of heterozygosity in each amplicon. The heterozygous amplicons thus identified are further sequenced to detect mutations. See, e.g., Cao et al., *Breast Cancer Res Treat.*, 114(3):457-62 (2009). Alternatively, high resolution melting analysis is becoming more and more popular in mutations scanning, and can also be used in the methods of the present invention. Like dHPLC, PCR amplification is used to produce amplicons from the target gene, and each amplicon is analyzed by high resolution melting analysis to detect the presence or absence of heterozygosity in each amplicon. The heterozygous amplicons thus identified are further sequenced to detect mutations. See, e.g., Jiménez et al., *Clin Biochem.*, 42(15):1572-6 (2009).

Alternatively, the restriction fragment length polymorphism (RFLP) and AFLP method may also prove to be useful techniques. In particular, if a mutations in the target nucleic acid region results in the elimination or creation of a restriction enzyme recognition site, then digestion of the target DNA with that particular restriction enzyme will generate an altered restriction fragment length pattern. Thus, a detected RFLP or AFLP will indicate the presence of a mutation.

Another useful approach is the single-stranded conformation polymorphism assay (SSCA), which is based on the altered mobility of a single-stranded target DNA spanning the mutations of interest. A single nucleotide change in the target sequence can result in different intramolecular base pairing pattern, and thus different secondary structure of the single-stranded DNA, which can be detected in a non-denaturing gel. See Orita et al., *Proc. Natl. Acad. Sci. USA*, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., *Biotechniques*, 5:1016-24 (1999); Sheffield et al., *Am. J. Hum. Genet.*, 49:699-706 (1991); Wartell et al., *Nucleic Acids Res.*, 18:2699-2705 (1990); and Sheffield et al., *Proc. Natl. Acad. Sci. USA*, 86:232-236 (1989). In addition, the double-strand conformation analysis (DSCA) can also be useful in the present invention. See Arguello et al., *Nat. Genet.*, 18:192-194 (1998).

The presence or absence of a mutation at a particular locus in a genomic region of an individual can also be detected using the amplification refractory mutation system (ARMS) technique. See e.g., European Patent No. 0,332,435; Newton et al., *Nucleic Acids Res.*, 17:2503-2515 (1989); Fox et al., *Br. J. Cancer,* 77:1267-1274 (1998); Robertson et al., *Eur. Respir. J.*, 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., *Clin. Chem.* 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., *Genomics,* 8:684-692 (1990); Shumaker et al., *Hum. Mutat.*, 7:346-354 (1996); Chen et al., *Genome Res.*, 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science,* 241:1077-1080 (1988); Chen et al, *Genome Res.*, 8:549-556 (1998); Iannone et al., *Cytometry,* 39:131-140 (2000). Thus, for example, to detect a single-nucleotide mutation at a particular locus in a genomic region, two oligonucleotides can be synthesized, one having the genomic sequence just 5' upstream from the locus with its 3' end nucleotide being identical to the nucleotide in the variant locus, the other having a nucleotide sequence matching the genomic sequence immediately 3' downstream from the variant locus. The oligonucleotides can be labeled for the purpose of detection. Upon hybridizing to the target nucleic acid under a stringent condition, the two oligonucleotides are subject to ligation in the presence of a suitable ligase. The ligation of the two oligonucleotides would indicate that the target DNA has a mutation at the locus being detected.

Detection of mutation can also be accomplished by a variety of hybridization-based approaches. Allele-specific oligonucleotides are most useful. See Conner et al., *Proc. Natl. Acad. Sci. USA,* 80:278-282 (1983); Saiki et al, *Proc. Natl. Acad. Sci. USA,* 86:6230-6234 (1989). Oligonucleotide probes (allele-specific) hybridizing specifically to an allele having a particular mutation at a particular locus but not to other alleles can be designed by methods known in the art. The probes can have a length of, e.g., from 10 to about 50 nucleotide bases. The target DNA and the oligonucleotide probe can be contacted with each other under conditions sufficiently stringent such that the mutations can be distinguished from the alternative variant/allele at the same locus based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular mutation.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, *Human Genetics*, 42:726 (1988). Alternatively, in a RNase protection assay, a RNA probe can be prepared spanning the mutations site to be detected and having a detection marker. See Giunta et al., *Diagn. Mol. Path.*, 5:265-270 (1996); Finkelstein et al., *Genomics*, 7:167-172 (1990); Kinszler et al., *Science* 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., *Nucleic Acids Res.*, 25:3377-3378 (1997).

A great variety of improvements and variations have been developed in the art on the basis of the above-described basic techniques, and can all be useful in detecting mutations in the present invention. For example, the "sunrise probes" or "molecular beacons" utilize the fluorescence resonance energy transfer (FRET) property and give rise to high sensitivity. See Wolf et al., *Proc. Nat. Acad. Sci. USA*, 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., *Nucleic Acids Res.*, 25:2516-2521 (1997); Rychlik et al., *Nucleic Acids Res.*, 17:8543-8551 (1989); Sharkey et al., *Bio/Technology* 12:506-509 (1994); Tyagi et al., *Nat. Biotechnol.*, 14:303-308 (1996); Tyagi et al., *Nat. Biotechnol.*, 16:49-53 (1998). The homo-tag assisted non-dimer system (HANDS) can be used in combination with the molecular beacon methods to suppress primer-dimer accumulation. See Brownie et al., *Nucleic Acids Res.*, 25:3235-3241 (1997).

Dye-labeled oligonucleotide ligation assay is a FRET-based method, which combines the OLA assay and PCR. See Chen et al., *Genome Res.* 8:549-556 (1998). TaqMan is another FRET-based method for detecting mutations. A TaqMan probe can be oligonucleotides designed to have the nucleotide sequence of the human nucleic acid spanning the variant locus of interest and to differentially hybridize with different alleles. The two ends of the probe are labeled with a quenching fluorophore and a reporter fluorophore, respectively. The TaqMan probe is incorporated into a PCR reaction for the amplification of a target nucleic acid region containing the locus of interest using Taq polymerase. As Taq polymerase exhibits 5'-3' exonuclease activity but has no 3'-5' exonuclease activity, if the TaqMan probe is annealed to the target DNA template, the 5'-end of the TaqMan probe will be degraded by Taq polymerase during the PCR reaction thus separating the reporting fluorophore from the quenching fluorophore and releasing fluorescence signals. See Holland et al., *Proc. Natl. Acad. Sci. USA*, 88:7276-7280 (1991); Kalinina et al., *Nucleic Acids Res.*, 25:1999-2004 (1997); Whitcombe et al., *Clin. Chem.*, 44:918-923 (1998).

In addition, the detection in the present invention can also employ a chemiluminescence-based technique. For example, an oligonucleotide probe can be designed to hybridize to either the wild-type or a variant locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., *Nucleic Acids Res.*, 24:4998-5003 (1996).

The detection of mutations for the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., *Electrophoresis*, 20:1171-1176 (1999).

Another useful technique that is gaining increased popularity is mass spectrometry. See Graber et al., *Curr. Opin. Biotechnol.*, 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., *Nat. Med.*, 3:360-362 (1997).

In addition, the microchip or microarray technologies are also applicable to the detection method of the present invention as will be apparent to a skilled artisan in view of this disclosure. For example, to genotype an individual, genomic DNA isolated from the individual can be prepared and hybridized to a DNA microchip having probes designed based on the target gene sequence.

As is apparent from the above survey of the suitable detection techniques, it may or may not be necessary to amplify the target DNA, i.e., the genomic region of interest, or the corresponding cDNA or mRNA to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual*, $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.*, 34:901-907 (1996); Collins et al., *Nucleic Acids Res.*, 25:2979-2984 (1997); Horn et al., *Nucleic Acids Res.*, 25:4835-4841 (1997);

Horn et al., *Nucleic Acids Res.*, 25:4842-4849 (1997); Nilsen et al., *J. Theor. Biol.*, 187:273-284 (1997).

In yet another technique for detecting mutations, the Invader® assay utilizes a novel linear signal amplification technology that improves upon the long turnaround times required of the typical PCR DNA sequenced-based analysis. See Cooksey et al., *Antimicrobial Agents and Chemotherapy* 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader® system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., *Nat. Biotechnol.*, 17:292-296 (1999).

The rolling circle method is another method that avoids exponential amplification. Lizardi et al., *Nature Genetics*, 19:225-232 (1998) (which is incorporated herein by reference). For example, Sniper™, a commercial embodiment of this method, is a sensitive, high-throughput SNP scoring system designed for the accurate fluorescent detection of specific variants. For each mutation, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, *Life Science News* 6, 2000, *Amersham Pharmacia Biotech* (2000).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., *Anal. Chem.*, 69:4703-4707 (1997). The fluorescence correlation spectroscopy is based on the spatio-temporal correlations among fluctuating light signals and trapping single molecules in an electric field. See Eigen et al., *Proc. Natl. Acad. Sci. USA*, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.*, 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a mutation in a genomic region of a particular individual should be apparent to a skilled artisan apprised of this disclosure.

Protein-based detection techniques may also prove to be useful, especially when the mutations causes amino acid substitutions or deletions or insertions or frameshift that affect the protein primary, secondary or tertiary structure. To detect the amino acid variations, protein sequencing techniques may be used. Alternatively, the recently developed HPLC-microscopy tandem mass spectrometry technique can be used for determining the amino acid sequence variations. See Gatlin et al., *Anal. Chem.*, 72:757-763 (2000).

Other useful protein-based detection techniques include immunoaffinity assays based on antibodies selectively immunoreactive with mutant proteins or specifically with wild-type proteins. Antibodies can be used to immunoprecipitate specific proteins from solution samples or to immunoblot proteins separated by, e.g., polyacrylamide gels. Immunocytochemical methods can also be used in detecting specific protein in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

The antibodies (or fragments thereof) useful in the present invention can be employed histologically—e.g., IHC, immunofluorescence or immunoelectron microscopy—for in situ detection of peptides encoded by nucleic acids of interest. In situ detection can be accomplished by removing a histological specimen from a patient, and applying thereto a labeled antibody of the present invention. The antibody (or its fragment) is preferably applied by overlaying the labeled antibody (or fragment) onto a biological sample. Through the use of such a procedure, it is possible to determine not only the presence and amount of the expression product of a target gene, but also its distribution in the examined tissue. Using the present invention, a skilled artisan will readily perceive that any of a wide variety of histological methods (e.g., staining procedures) can be modified to achieve such in situ detection.

U.S. Pat. No. 5,965,377 discloses an antibody-based method for determining the presence of mutated protein in cells expressing the protein, wherein the normal protein contains amino-terminus and carboxy-terminus regions and wherein the mutated protein is typically a foreshortened protein from which carboxy-terminus regions are missing. This method can be adapted to detect truncation mutations in the target gene of the present invention. Specifically, an antibody reactive with the N-terminus of the target protein and an antibody reactive with the C-terminus of the target protein are used to react with a cell sample, and the ratio between the reactivity with the C-terminus and N-terminus can be obtained. If the reactivity with the C-terminus is about zero or no greater than about half of the reactivity with the N-terminus in the sample, it would indicate the presence of a truncation mutation in the gene. The antibody reactivity can be measured by any suitable immunoassays, e.g., immunohistochemistry (IHC) and ELISA.

The antibody based methods described above can also be used to determine generally the expression level of the target gene, PALB2, as will be apparent to skilled artisan.

For purposes of detecting a reduced level of gene expression, either mRNA or protein level in a sample from a patient can be determined by conventional methods known in the art.

Protein expression level in a sample can be determined using an immunoassay described above. For mRNA level, typically hybridization of DNA probes or primers is utilized. For example, for mRNA expression level, qRT-PCT can be used. mRNA can be isolated from a particular sample, and the target gene mRNA, and preferably in addition, a reference gene mRNA (typically a housekeeping gene), are amplified by qRT-PCR, and the relative amount of the target gene mRNA is determined, which is compared to a predetermined reference standard level (e.g., an average level determined in a plurality of normal samples). Alternatively, digital PCR is also useful.

Additionally, gene expression level can also be detected indirectly by determining the methylation status of the target gene. If the target gene is methylated at a greater extent than normal, then the target gene expression is usually reduced. Methods for determining gene methylation status are well known in the art.

The present invention also provides kits for use in the methods of the present invention. The kits may include a carrier for the various components of the kits. The carrier can be a container or support, in the form of, e.g., bag, box, tube, rack, and is optionally compartmentalized. The carrier may define an enclosed confinement for safety purposes during shipment and storage. The kit also includes various components useful in detecting mutations, or determining gene expression (mRNA and protein) levels, using the above-discussed detection techniques. For example, the detection kit may include one or more oligonucleotides useful as primers for amplifying all or a portion of the PALB2 genomic or cDNA. The detection kit may also include one or more oligonucleotide probes for hybridization to the PALB2 genomic or cDNA or mRNA. Optionally the oligonucleotides are affixed to a solid support, e.g., incorporated in a microchip or microarray included in the kit.

In some embodiments of the invention, the detection kit contains one or more antibodies selectively immunoreactive with PALB2 protein, for example antibodies selectively immunoreactive with the N-terminus of PALB2 protein, and/or antibodies selectively immunoreactive with the C-terminus of PALB2 protein.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit should include instructions on using the kit for the various methods of the present invention as described above.

As discussed above, the present invention provides a method of predicting an individual's response to therapy for pancreatic cancer, and a method of treating pancreatic cancer. For example, in one embodiment, once a patient is identified as having a germline or somatic mutation in a PALB2 gene or a reduced level of PALB2 gene expression, the patient is treated with a therapy that induces DNA double-strand breaks (DSB) or interferes with DNA double-strand breaks (DSB) repairs by homologous recombination in tumor cells. Many therapies are known in the art that "induce DNA double-strand breaks (DSB) or interfere with DNA double-strand breaks (DSB) repairs by homologous recombination in tumor cells". For example, radiation therapy induces DNA damages including DNA double-strand breaks. Chemotherapeutics such as DNA damaging agents are also useful including, but not limited to, alkylating agents and topoisomerase inhibitors, which are designed to damage DNA in order to prevent cancer cells from reproducing.

Alkylating agents attach an alkyl group ($C_nH_{2n+1}$) to DNA causing DNA damages. Examples of alkylating agents include nitrogen mustards such as cyclophosphamide, mechlorethamine, uramustine, melphalan, chlorambucil, and ifosfamide; nitrosoureas such as carmustine, lomustine, streptozocin, alkyl sulfonates, and busulfan; platinum agents such as cisplatin, carboplatin, nedaplatin, oxaliplatin, satraplatin, triplatin tetranitrate and picoplatin; procarbazine; altretamine; tetrazines such as dacarbazine, mitozolomide and temozolomide; and antibiotics such as mitomycins, particularly mitomycin C.

Topoisomerase inhibitors inhibit the activity of topoisomerase enzymes (topoisomerase I and II), and interfere with the catalyzing the breaking and rejoining of the phosphodiester backbone of DNA strands during DNA replication and cell division. Examples of topoisomerase inhibitors include topoisomerase i inhibitors such as irinotecan, topotecan, camptothecin and D; topoisomerase ii inhibitors such as etoposide and doxorubicin.

In addition, inhibitors of DNA repair enzymes (e.g., PARP inhibitors) are also particularly effective in treating PALB2 defective pancreatic cancer. PARP (poly (ADP-ribose) polymerase) is a ubiquitous nuclear enzyme that is involved in DNA damage repairs. Examples of PARP inhibitors include BSI-201 by BiPar Sciences Inc. (*Clin. Cancer Res.*, 15(20): 6367-77 (2009)); olaparib (AZD2281) by AstraZeneca (*N. Engl. J. Med.*, 361(2):123-34 (2009)), ABT-888 by Abbott Laboratories, Inc. (*J. Clin. Oncol.*, 27(16):2705-11 (2009), and AG014699 by Pfizer Inc. (*Clin. Cancer Res.*, 14(23): 7917-23 (2008)).

Thus, in some embodiments of the present invention, a method of predicting an individual's response to therapy comprises detecting in a sample obtained from an individual, a mutation in the PALB2 gene, wherein the presence of the mutation would indicate that the individual has an increased likelihood of responding to a therapy that comprises radiation, an alkylating agent, a topoisomerase inhibitor, and/or a PARP inhibitor. In specific embodiments, the therapy comprises at least one mitomycin C, cisplatin, carboplatin, oxaliplatin, and a PARP inhibitor (e.g., BSI-201 or olaparib).

In some embodiments, the treatment method of the present invention comprises detecting, in a patient, a mutation in the PALB2 gene or a reduced PALB2 gene expression, and in the presence of such a mutation or reduced gene expression, treating the patient with a therapy that comprises radiation, an alkylating agent, a topoisomerase inhibitor, and/or a PARP inhibitor. In specific embodiments, the therapy comprises at least one mitomycin C, cisplatin, carboplatin, oxaliplatin, and a PARP inhibitor (e.g., BSI-201 or olaparib).

EXAMPLE 1

Exomic Sequencing Identifies PALB2 as a Pancreatic Cancer Susceptibility Gene

We have sequenced the entire genomes of five individuals. In addition, 68 patients have been evaluated for tumor-specific mutations in all exons of protein coding genes (exomic sequencing). This coincidentally yielded information about germline sequence variations in these individuals. To explore the utility of such information, we evaluated a pancreatic cancer patient (Pa10) whose tumor DNA had been sequenced. This patient had familial pancreatic cancer, as defined by the fact that his sister also had developed the disease.

Among the 20, 661 coding genes analyzed, we identified 15,461 germline variants in Pa10 not found in the reference human genome. Of these, 7318 were synonymous, 7721 were missense, 64 were nonsense, 108 were at splice sites, and 250 were small deletions or insertions (54% in-frame). Past studies have shown that tumors arising in patients with a hereditary predisposition harbor no normal alleles of the responsible gene: one allele is inherited in mutant form, often producing a stop codon, and the other (wild type) allele is inactivated by somatic mutation during tumorigenesis. In Pa10, only three genes met these criteria: SERPINB12, RAGE and PALB2. Of these, we considered PALB2 to be the best candidate because germline stop codons in SERPINB12 and RAGE, but not in PALB2, are relatively common in healthy individuals and because germline PALB2 mutations have previously been associated with breast cancer predisposition and Fanconi anemia although its function is not well understood. Pa10 harbored a germline deletion of 4 by (TTGT at c.172-175) producing a frameshift at codon 58; the pancreatic cancer that developed in Pa10 had also somatically acquired a transition mutation (C to T) at a canonical splice site for exon 10 (IVS10+2).

To determine whether PALB2 mutations occur in other patients with familial pancreatic cancer, we sequenced this gene in a cohort of 96 familial pancreatic cancer patients, 90 of which were of Caucasian ancestry. Sixteen of these patients had one first degree relative with pancreatic cancer and 80 had at least two additional relatives, at least one of which was first degree, with the disease. Truncating mutations were identified in three of the 96 patients, each producing a different stop codon (FIG. 1). The average age-of-onset of pancreatic cancer in these families was 66.7 years, similar to the mean age of onset of 65.3 years in the families without PALB2 mutations. We determined the germ-line sequence of an affected brother in one of these kindreds, and he harbored the same stop codon. Truncating mutations in PALB2' are rare in individuals without cancer; none have been reported among 1,084 normal individuals in a previous study using a cohort of similar ethnicity to ours. While some families we identified with a PALB2 stop mutation had a history of both breast and pancreatic cancer, breast cancer was not observed in all families. From these data, PALB2 appears to be the second most commonly mutated gene for hereditary pancreatic cancer. Interestingly, the most commonly mutated gene is BRCA2, whose protein product is a binding partner for the PALB2 protein.

In summary, through complete, unbiased sequencing of protein-coding genes, we have discovered a gene responsible for a hereditary disease. We note that this approach is independent of classical methods for gene discovery, such as linkage analysis, which can be challenging in the absence of large families with monogenic diseases. We predict that variations of the approach described here will soon become a standard tool for the discovery of disease-related genes.

EXAMPLE 2

PALB2 Mutations and Response to DNA Damaging Agents in Pancreatic Cancer

We report here a patient with gemcitabine resistant pancreatic cancer for whom mitomycin C treatment, selected based on its preclinical activity in a personalized xenograft generated from the patient's surgically resected tumor, resulted in long lasting (36+ months) cancer control. Global genetic sequencing revealed biallelic inactivation of the PALB2 gene in this patient's cancer that disrupts BRCA1 and 2 interactions. This work suggests that inactivation of PALB2 is a determinant of response to DNA damage in pancreatic cancer and a new target for personalizing cancer treatment. Integrating personalized xenografts with unbiased genomic sequencing led to individualized treatment and the identification of a new biomarker of drug response.

The patient described in this report was enrolled in the J0507 Johns Hopkins Medical Institute clinical trial (NCT00276744). This is a pilot prospective clinical trial in which patients with resectable pancreatic cancer operated at the Johns Hopkins Hospital consent to have a portion of their resected tumor implanted and propagated in nude mice. These xenografted tumors are treated with a set of anticancer agents with the goal to identify the most effective agents that can be used to treat the patient's cancer.

Six-week-old female athymic nude mice (Harlan, Ind., US) are implanted with tumor tissues collected at the time of surgery. The research protocol was approved by the Johns Hopkins University Animal Care and Use Committee and animals were maintained in accordance to guidelines of the American Association of Laboratory Animal Care. The detail process for generation of xenografts and treatment protocols has been published elsewhere. Rubio-Viqueira et al., *Clin. Cancer Res.*, 12(15):4652-61 (2006). Tumors were allowed to grow until reaching ~200 mm$^3$, at which time mice were randomized to: 1) Control; 2) MMC 5 mg/Kg/ip single dose; or 3) cisplatin 6 mg/Kg single dose, with 5-6 mice (10 evaluable tumors) in each group. Tumor size was evaluated two times per week by caliper measurements using the following formula: tumor volume=[length X width$^2$]/2. Relative tumor growth inhibition was calculated by relative tumor growth of treated mice divided by relative tumor growth of control mice since the initiation of therapy (T/C).

Genomic analysis. The sequences of 23,219 transcripts representing 20,661 protein-coding genes in the patient's cancer were determined. Whenever a variant was identified in the cancer, the patient's germline was also sequenced, revealing information about the germline variations in this patient.

Co-immunoprecipitation. To assess BRCA1 and BRCA2 nuclear binding a co-immunoprecipitation assay was performed using a commercially available kit (Thermo Scientific #23600, Waltham, Mass.). Samples from tumor JH033, sensitive to MMC and Panc185, resistant to MMC were used. Monoclonal antibody OP107 against BRCA1, purchased from Calbiochem (San Diego, La.), was used to immunoprecipitate the BRCA1/2 complex. After stabilization of the antibodies to the resin by a covalent union, the samples were added and incubated for 24 hours. Samples were eluted, electrophoresed and further immunoblotted with mAB against BRCA1 (OP107) and BRCA2 (OP95) purchased from Calbiochem (San Diego, La.).

Western Blot Analysis. Tumor tissues (75 mg/mouse) from control and treated with MMC were minced on ice in pre-chilled lysis buffer. 30 μg of sample was electrophoresed and further electrotransfered to Immobilon-P membranes (Millipore, Bedford, Mass.). Primary antibodies for BRCA1 (OP107), BRCA2 (OP95), or PALB2 (2134.00.02) from Strategic Scientific Inc. (Newark, Del.) and FANCD2 (4945) from Cell Signaling (Danvers, Mass.) were used to blot the membranes.

Figure 2A:
FIG. 2A is a chest CT image obtained in the first postoperative visit showing an enlarged left supracalvicular node (arrow). A biopsy of this node showed metastatic adenocarcinoma.
Figure 2B:
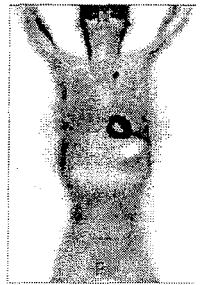
FIG. 2B is an image of FDG-PET scan demonstrating increase glucose update in the above mentioned node (arrow)
Figure 2C:
FIG. 2C demonstrates extensive locoregional recurrent disease after for cycles of gemcitabine.

Results: Clinical Case. A 61 year-old male, with family history of pancreatic cancer, who had been previously tested and found to be wild-type for the BRCA2 gene, underwent a distal pancreatectomy and splenectomy for a pT3N1M0 infiltrating ductal adenocarcinoma of the pancreas. The patient had a 4 cm, poorly differentiated adenocarcinoma that had metastatized to 8 of 26 resected lymph nodes with prominent extranodal extension. Venous and perineural invasion were identified and the carcinoma extended to involve the celiac artery margin of resection. The patient was enrolled in J0507 and a portion of the surgically resected tumor, coded as JH033, was xenografted in nude mice. Two months after surgery, prior to initiating adjuvant treatment, the patient was found to have a biopsy proven metastasis to a supraclavicular lymph node and his CA 19-9 rose to 10,132 U/ml (FIGS. 2A and B). The patient was treated with single agent gemcitabine but developed significant disease progression after 4 months with pleural effusion, loco-regional progression in the abdominal cavity, and a CA 19-9 of 98,405 U/ml (FIGS. 2C and D).

Figure 2D:
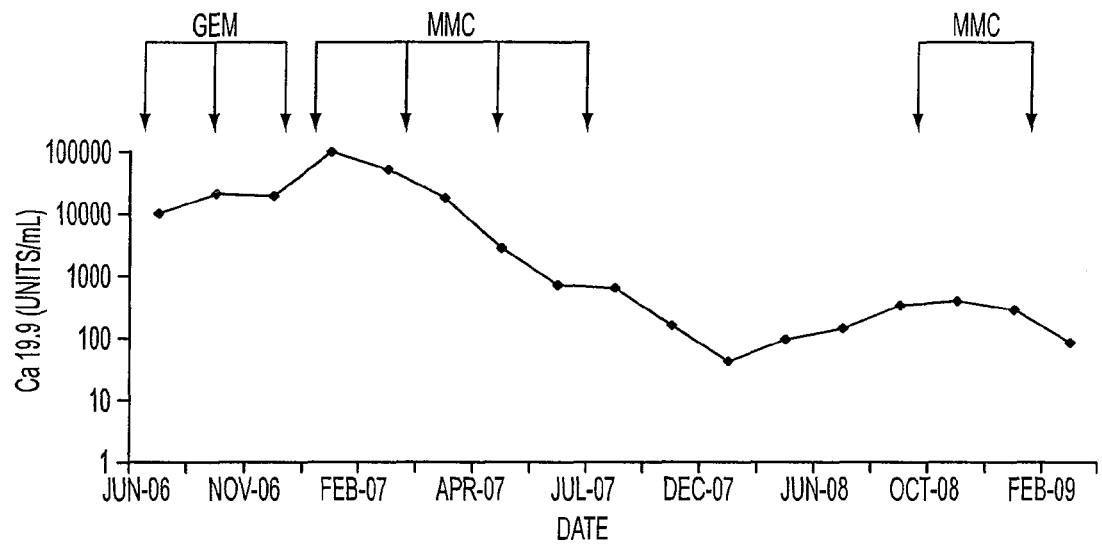
FIG. 2D is a plot showing the time-course of CA 19-9 indicating disease progression while on gemcitabine and complete normalization with MMC.
Figure 2E:
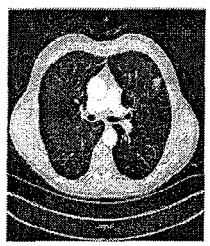
FIG. 2E demonstrates late pulmonary progression with a left upper lesion after 22 months of follow up.
Figure 2F:
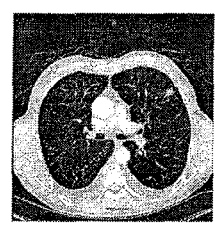
FIG. 2F indicates decrease in pulmonary lesion size after two additional courses of MMC.

At this time, the results of the xenograft treatment studies became available (FIG. 2A), and based on the response of the patient's xenografted cancer to MMC, the patient was treated with MMC 8 mg/m$^2$/28 days for a total of five courses. After treatment with MMC the CT scan findings improved and the CA 19-9 level normalized (FIG. 2D). This response was maintained for 22 months, after which the CA 19-9 rose to 392 U/ml and a new lung nodule developed in the left upper lobe (FIG. 2E). The patient was treated with 2 additional cycles of MMC with biochemical and CT scan response (FIGS. 2D and F) but developed incipient renal failure. Because the xenograft was also sensitive to cisplatin, platinum-based chemotherapy was initiated and the patient received three cycles of this agent. At his last follow up, three years after surgical resection, his CA 19-9 is 39 U/ml and the patient remains asymptomatic.

Figure 3:
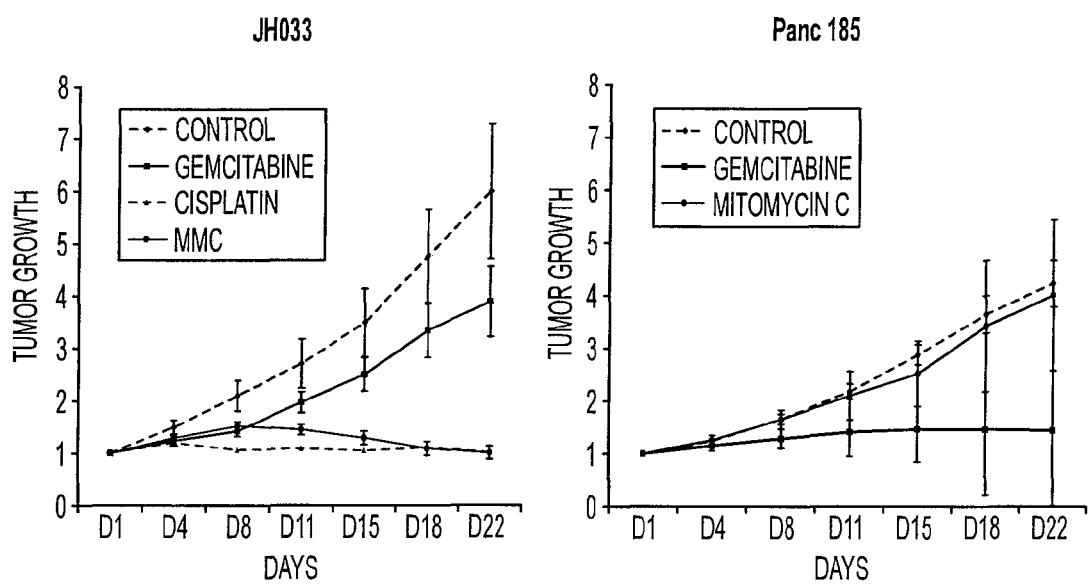
FIG. 3 includes tumor growth curves from in vivo xenograft studies indicating resistance to gemcitabine and remarkable response to MMC and cisplatin in the patient's own xenograft. Panc 185 tumor with wild-type PALB2 is presented as a control.

Mechanism underlying unique sensitivity to DNA damaging agents. This patient tumor was recently sequenced as a part of an effort to sequence the pancreatic cancer genome. The results of this sequencing allowed us to assess, in an unbiased fashion, potential genetic determinants of this patient's remarkable response to MMC. His carcinoma was found to have a somatically acquired transition mutation (C to T) at a canonical splice site for exon 10 (IVS10+2) in the PALB2 gene (FIG. 3A). A subsequent study identified a germline deletion of 4 base pairs (TTGT at ~172 to 175) that produced a frameshift mutation at codon 58 of PALB2. The PALB2 gene was therefore biallelically inactivated in this patient's cancer. Functional analysis demonstrated that this tumor has an intact FA complex 1 system leading to successful mono-ubiquitination of the FANCD2 protein (FIG. 3B, first lane) similar to the Panc 185 tumor used as a control that has a wild-type PALB2 gene and is resistant to MMC. The biallelic inactivation of PALB2 in our patient's tumor disrupts the interaction between the complex BRCA1/BRCA2, which is essential for double strand break repair (FIG. 3C).

Thus, we have described herein the remarkable clinical outcome of a patient with advanced, gemcitabine resistant, pancreatic cancer who was treated with DNA damaging agents based on the observation of significant activity of this class of agents against a personalized xenograft generated from the patients own tumor. Nearly complete sequencing of all of the coding genes in this patient's cancer revealed biallelic inactivation of PALB2, a DNA repair gene, loss of which mechanistically explains the observed sensitivities of the patient's cancer. This study highlights the potential power of global genomic sequencing for the discovery of novel markers of drug activity.

We report that an unbiased genomic sequencing of a patient's tumor led to the discovery of a genetic defect that explains the unique susceptibility of this patient's tumor to DNA damaging agents. B1allelic inactivation of the PALB2 gene alters the interaction of the BRCA1 and 2 proteins, required for proper functioning of the DNA damage repair pathway. Zhang et al., *Curr. Biol.*, 19(6):524-9 (2009). Response of pancreatic cancer to DNA damaging agents can now be predicted by sequencing the PALB2 and BRCA2 genes. This situation is analogous to the EGFR gene mutations in lung cancer and response to EGFR inhibitors. It is likely that this is a generalizable phenomenon and extreme, clinically significant predictors of patient-specific responses to anticancer agents will be identified as additional cancers are sequenced. Importantly, the process presented here can be escalated and systematically used to discover rare, albeit clinically relevant, genetic defects that confer a vulnerability to therapeutic interventions. As the ability to obtain global genomic information from individual patient tumors becomes cheaper and more easily obtainable, living tumor xenografts with validated clinical response will become a viable platform to systematically explore "connections" between drug response and genetic determinants of response.

In summary, we describe here a patient with poor prognosis pancreatic cancer for whom a personalized xenograft model generated from the patient's own tumor, linked to global genomic sequencing, led to the discovery of a highly effective treatment regimen as well as the genetic defect explaining the observed sensitivity of this patient's cancer to DNA damaging agents. This approach forms the basis for linking personalized xenografts with global genomic sequencing for the development of personalized treatment and biomarker discovery.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

We claim:

1. A method of administering a therapy to a human with a pancreatic cancer, comprising:
   testing and detecting in a sample obtained from the human with a pancreatic cancer the presence of a mutation in the PALB2 gene selected from the group consisting of: 172-5 del TTGT; IVS5-1 G>T; 3256 C>T, and IVS10+2 C>T; and
   administering to said human a therapy that induces DNA damage or interferes with DNA damage repair in tumor cells.

2. The method of claim 1 wherein said therapy is radiation therapy.

3. The method of claim 1 wherein said therapy is a DNA damaging agent.

4. The method of claim 1 wherein said therapy is an inhibitor of a DNA repair enzyme.

5. The method of claim 1 wherein said therapy comprises treatment with a PARP inhibitor.

6. The method of claim 1 wherein said sample is a normal tissue sample.

7. The method of claim 1 wherein the human has a family history of pancreatic cancer.

* * * * *